United States Patent
Ogura et al.

(10) Patent No.: US 9,592,026 B2
(45) Date of Patent: Mar. 14, 2017

(54) X-RAY CT APPARATUS, RECONSTRUCTION ARITHMETIC DEVICE, AND RECONSTRUCTION ARITHMETIC METHOD

(71) Applicant: HITACHI, LTD., Tokyo (JP)

(72) Inventors: Yuta Ogura, Tokyo (JP); Ryota Kohara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/778,299

(22) PCT Filed: Mar. 13, 2014

(86) PCT No.: PCT/JP2014/056654
§ 371 (c)(1),
(2) Date: Sep. 18, 2015

(87) PCT Pub. No.: WO2014/167935
PCT Pub. Date: Oct. 16, 2014

(65) Prior Publication Data
US 2016/0278733 A1  Sep. 29, 2016

(51) Int. Cl.
*G06K 9/00* (2006.01)
*A61B 6/00* (2006.01)
(Continued)

(52) U.S. Cl.
CPC .............. *A61B 6/582* (2013.01); *A61B 6/032* (2013.01); *A61B 6/0407* (2013.01); *A61B 6/461* (2013.01);
(Continued)

(58) Field of Classification Search
None
See application file for complete search history.

(56) References Cited

U.S. PATENT DOCUMENTS

| 5,831,736 A * | 11/1998 | Lichtman | G02B 21/22 250/559.22 |
| 8,054,094 B1 * | 11/2011 | Langoju | A61B 5/0536 324/705 |

(Continued)

FOREIGN PATENT DOCUMENTS

| JP | 2006-25868 | 2/2006 |
| JP | 2011-153976 | 8/2011 |

(Continued)

OTHER PUBLICATIONS

N S Paull, J Blobel2, E Prezelj1 , P Burey1 , A Ursani3, R J Menezes1, H Kashani4 and J H Siewerdsen5, The reduction of image noise and streak artifact in the thoracic inlet during low dose and ultra-low dose thoracic CT, Published Feb. 10, 2010 o 2010 Institute of Physics and Engineering in Medicine Physics in Medicine and Biology, vol. 55.*

(Continued)

*Primary Examiner* — Andrae S Allison
(74) *Attorney, Agent, or Firm* — Cooper & Dunham LLP

(57) ABSTRACT

In order to provide an X-ray CT apparatus or the like capable of improving the image quality even with low-exposure scanning by reducing artifacts generated around high absorbers on an image while reducing the amount of image noise, a reconstruction arithmetic device 221 sets the number of iterations of iterative processing for correcting projection data, and calculates, as calibration coefficients, a correction coefficient β and an adjustment coefficient α for adjusting the application ratio of noise reduction processing f1 and signal strength maintenance processing f2 included in the iterative processing. By performing the iterative processing including the noise reduction processing f1 and signal strength maintenance processing f2 on the projection data based on the number of iterations and the calibration (Continued)

coefficients α and β, corrected projection data is created, and a CT image is reconstructed.

11 Claims, 31 Drawing Sheets

(51) Int. Cl.
*A61B 6/03* (2006.01)
*G06T 11/00* (2006.01)
*A61B 6/04* (2006.01)
*G06K 9/46* (2006.01)
*G06T 7/00* (2006.01)

(52) U.S. Cl.
CPC .......... *A61B 6/5205* (2013.01); *A61B 6/5258* (2013.01); *G06K 9/4604* (2013.01); *G06T 7/0012* (2013.01); *G06T 11/005* (2013.01); *G06T 11/006* (2013.01); *G06T 2207/10081* (2013.01); *G06T 2211/424* (2013.01)

(56) References Cited

U.S. PATENT DOCUMENTS

| | | | | |
|---|---|---|---|---|
| 2003/0223532 | A1* | 12/2003 | Clinthorne | G01T 1/2928 378/19 |
| 2008/0219534 | A1* | 9/2008 | Faul | A61B 6/032 382/131 |
| 2008/0273656 | A1* | 11/2008 | Ziegler | G06T 11/005 378/19 |
| 2009/0324045 | A1* | 12/2009 | Grasruck | G06T 11/006 382/131 |
| 2010/0080430 | A1* | 4/2010 | Souza | G06T 7/0081 382/131 |
| 2010/0128958 | A1* | 5/2010 | Chen | A61B 6/032 382/132 |
| 2012/0020448 | A1* | 1/2012 | Khare | G06T 11/006 378/4 |
| 2012/0128265 | A1* | 5/2012 | Silver | G06T 11/006 382/275 |
| 2012/0155736 | A1* | 6/2012 | Faul | A61B 6/032 382/131 |
| 2012/0308104 | A1 | 12/2012 | Yang et al. | |

FOREIGN PATENT DOCUMENTS

| | | |
|---|---|---|
| JP | 2012-250043 | 12/2012 |
| WO | WO2013/008702 | 1/2013 |

OTHER PUBLICATIONS

M. T. Manhart et al., "Guided noise reduction with streak removal for high speed flat detector CT perfusion," 2013 IEEE Nuclear Science Symposium and Medical Imaging Conference (2013 NSS/MIC), Seoul, 2013, pp. 1-5.*

Tianfang et al, Noise Reduction for LowDose SingleSlice Helical CT Sinograms, IEEE Trans Nucl Sci. Jun. 2006; 53(3): 1230-1237.*

Patrick J. La Rivière, Member, IEEE, and David M. Billmire, Reduction of Noise-Induced Streak Artifacts in X-Ray Computed Tomography Through Spline-Based Penalized-Likelihood Sinogram Smoothing, IEEE Transactions on Medical Imaging, vol. 24, No. 1, Jan. 2005 105.*

International Search Report in PCT/JP2014/056654.

Jing Wang et al., "Penalized Weighted Least-Squares Approach to Sinogram Noise Reduction and Image Reconstruction for Low-Dose X-Ray Computed Tomography". IEEE Transactions on Medical Imaging, vol. 25, No. 10, Oct. 2006.

Ignace Loris et al., "On a generalization of the iterative soft-thresholding algorithm for the case of non-separable penalty". Universite Libre de Bruxelles, Aug. 5, 2011.

* cited by examiner

FIG.4
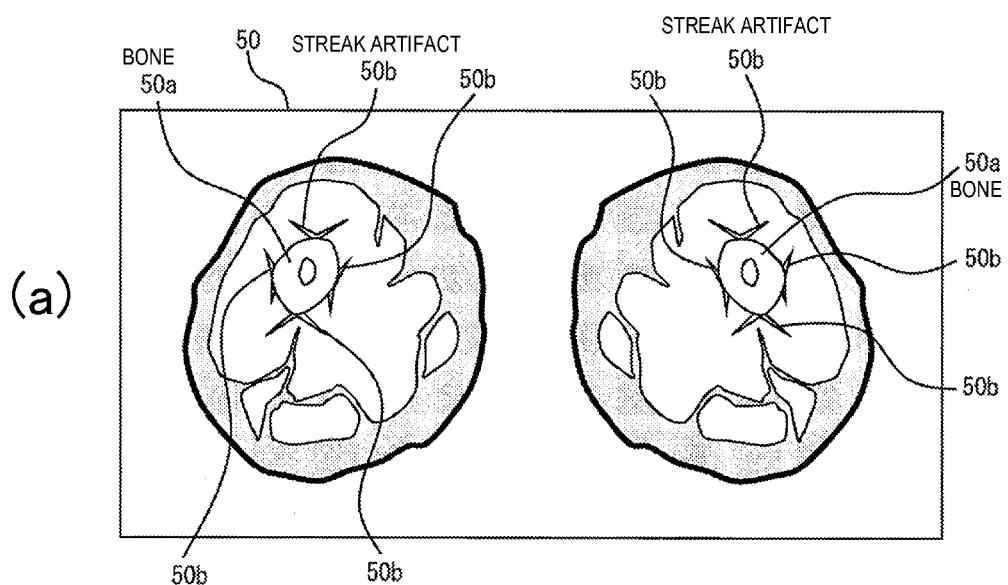
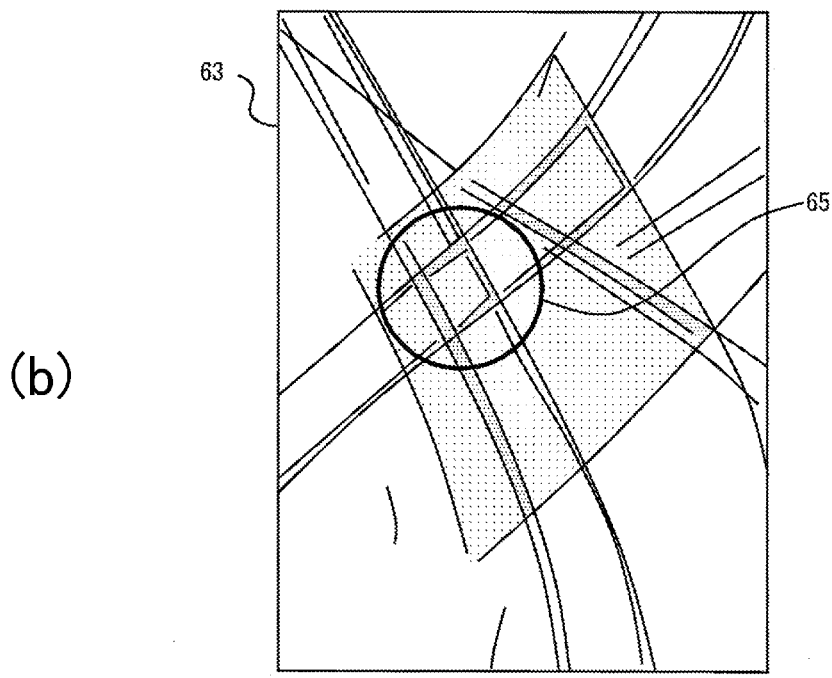

FIG.16
(a) 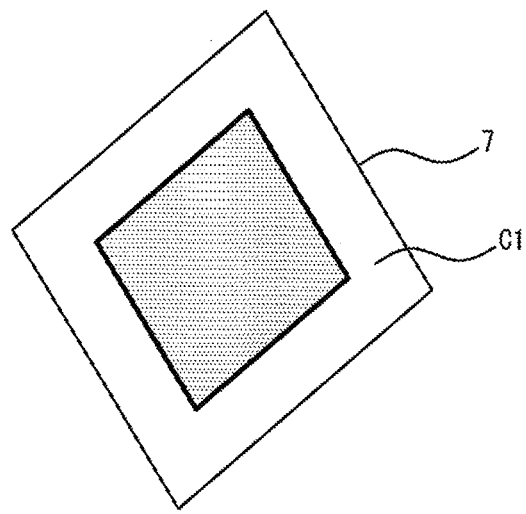
(b) 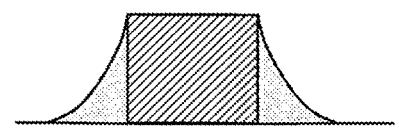
(c) 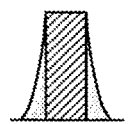

FIG.17
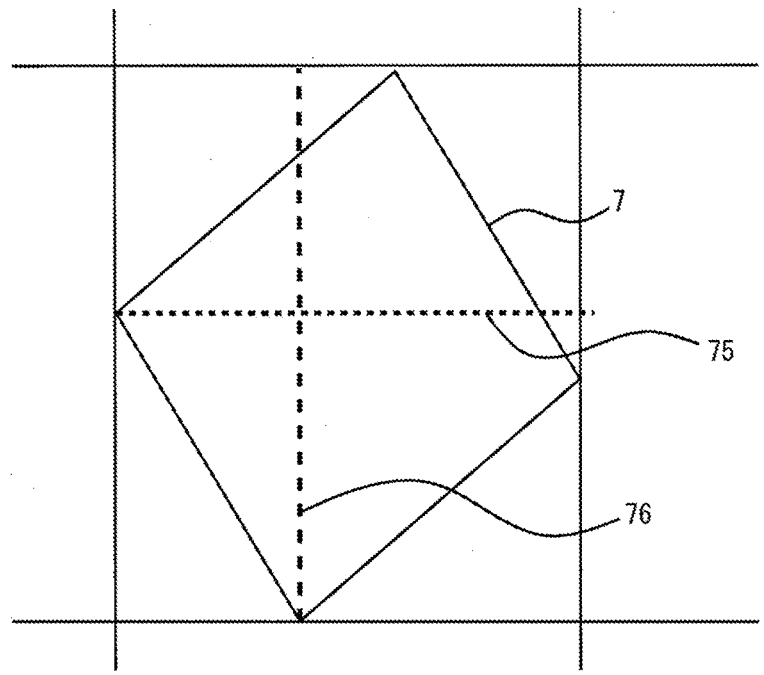
(a)
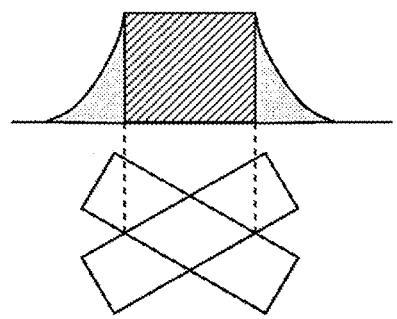
(b)
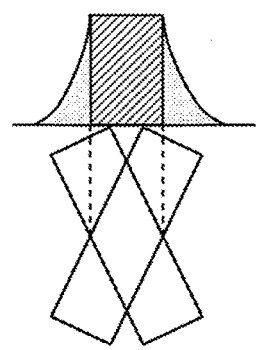
(c)

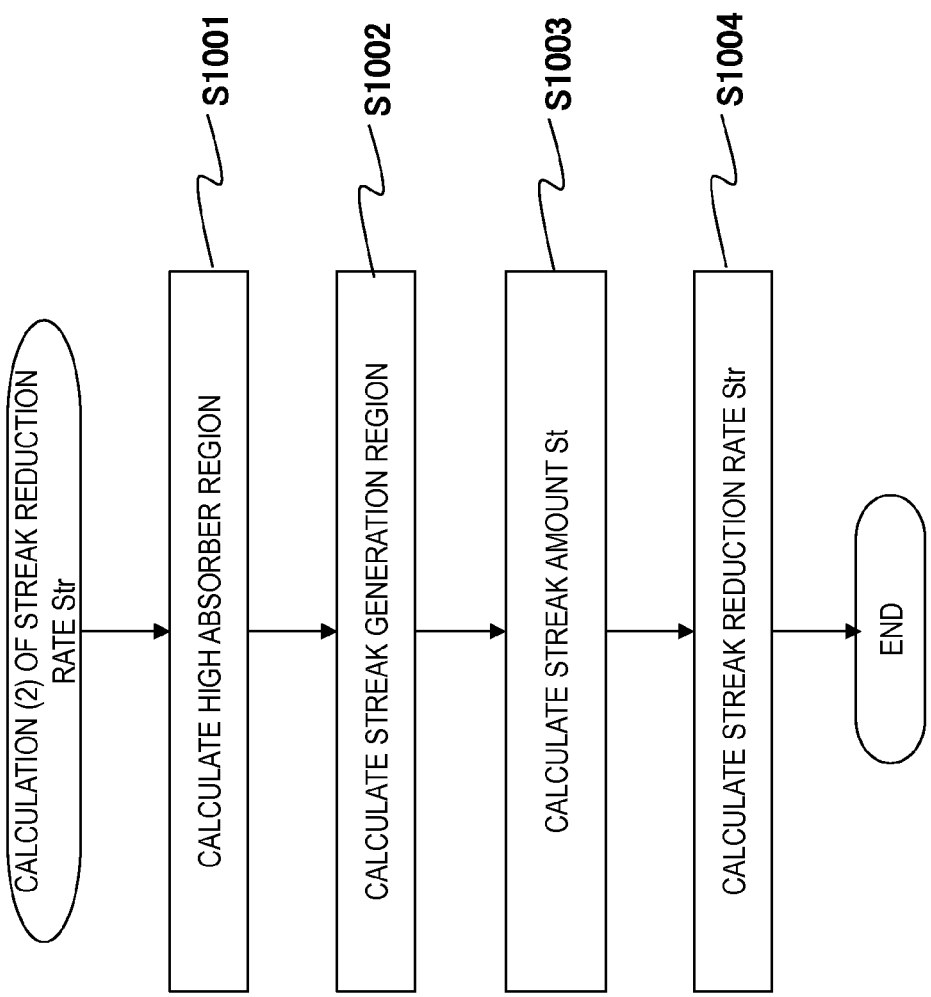

US 9,592,026 B2

X-RAY CT APPARATUS, RECONSTRUCTION ARITHMETIC DEVICE, AND RECONSTRUCTION ARITHMETIC METHOD

TECHNICAL FIELD

The present invention relates to an X-ray CT apparatus or the like to obtain a CT image by irradiating an object with X-rays. In particular, the present invention relates to the correction of projection data obtained by the X-ray CT apparatus.

BACKGROUND ART

In recent years, in order to perform a CT examination with low exposure dose, an X-ray CT apparatus for executing image reconstruction using a successive approximation method has been developed. Through the image reconstruction using the successive approximation method, a CT image with less noise is obtained even at low dose.

NPL 1 discloses successive approximation projection data correction processing that is one of the successive approximation methods. The successive approximation projection data correction processing is one of the projection data correction processing that is the pre-processing of image reconstruction. In the successive approximation projection data correction processing, update equation having the projection value of projection data as a variable is used. The update equation includes a smoothing coefficient (also referred to as a correction coefficient or a penalty term) indicating the strength of correction. In the successive approximation projection data correction processing, the projection value is iteratively updated using the above-described update equation.

CITATION LIST

Non Patent Literature

[NPL 1] Jing Wang et. al., "Penalized Weighted Least-Squares Approach to Sinogram Noise Reduction and Image Reconstruction for Low-Dose X-Ray Computed Tomography", IEEE TRANSACTIONS ON MEDICAL IMAGING, VOL. 25, NO. 10, October 2006, 1272-1283

[NPL 2] Jing Wang et. al., "Penalized Weighted Least-Squares Approach to Sinogram Noise Reduction and Image Reconstruction for Low-Dose X-Ray Computed Tomography", IEEE TRANSACTIONS ON MEDICAL IMAGING, VOL. 25, NO. 10, October 2006, 1272-1283)

[NPL 3] Ignace Loris and Caroline Verhoeven "On a generalization of the iterative soft-thresholding algorithm for the case of non-separable penalty" 2011 Inverse Problems 27 125007

SUMMARY OF INVENTION

Technical Problem

In the processing described in NPL 1 described above, however, when trying to obtain a high noise reduction effect, not only noise but also the signal strength of a high signal portion is reduced. In this case, the signal strength of an adjacent low signal portion is increased. As a result, a phenomenon that the edge portion of the signal becomes smooth occurs. This phenomenon becomes noticeable as a difference between the CT values in the channel direction of projection data increases. When performing image reconstruction using such projection data, there is a problem that streak artifacts are generated around a high absorber on the image. Therefore, when expecting a large noise reduction effect, the method disclosed in NPL 1 is insufficient in that the streak artifacts are generated.

The present invention has been made in view of the above problem, and it is an object of the present invention to provide an X-ray CT apparatus or the like capable of improving the image quality even with low-exposure scanning by reducing artifacts generated around the high absorber on the image while reducing the amount of image noise.

Solution to Problem

In order to achieve the above-described object, a first invention is an X-ray CT apparatus, including: an X-ray generator that emits X-rays from periphery of an object; an X-ray detector that detects X-rays transmitted through the object; a data acquisition system that acquires data detected by the X-ray detector; a reconstruction arithmetic device that creates projection data by receiving the data acquired by the data acquisition system and reconstructs a CT image using the projection data; and a display device that displays the CT image, in which the reconstruction arithmetic device includes: a number-of-iterations setting section that sets the number of iterations of iterative processing for correcting the projection data; a calibration coefficient calculating section that calculates a calibration coefficient for adjusting an application ratio of a first processing function and a second processing function having a different characteristic from the first processing function, the first and second processing functions being included in the iterative processing; a successive approximation projection data correction processing section that creates corrected projection data by performing the iterative processing on the projection data based on the number of iterations and the calibration coefficient; and an image reconstruction section that reconstructs the CT image using the corrected projection data.

A second invention is a reconstruction arithmetic device including: a number-of-iterations setting section that sets the number of iterations of iterative processing for correcting projection data; a calibration coefficient calculating section that calculates a calibration coefficient for adjusting an application ratio of a first processing function and a second processing function having a different characteristic from the first processing function, the first and second processing functions being included in the iterative processing; a successive approximation projection data correction processing section that creates corrected projection data by performing the iterative processing on the projection data based on the number of iterations and the calibration coefficient; and an image reconstruction section that reconstructs a CT image using the corrected projection data.

A third invention is a reconstruction arithmetic method including: a number-of-iterations setting step in which a reconstruction arithmetic device sets the number of iterations of iterative processing for correcting projection data; a calibration coefficient calculation step in which the reconstruction arithmetic device calculates a calibration coefficient for adjusting an application ratio of a first processing function and a second processing function having a different characteristic from the first processing function, the first and second processing functions being included in the iterative processing; a corrected projection data creation step in which the reconstruction arithmetic device creates corrected projection data by performing the iterative processing on the projection data based on the number of iterations and the calibration coefficient; and a reconstruction step in which the reconstruction arithmetic device reconstructs a CT image using the corrected projection data.

Advantageous Effects of Invention

According to the present invention, it is possible to provide an X-ray CT apparatus or the like capable of improving the image quality even with low-exposure scanning by reducing artifacts generated around the high absorber on the image while reducing the amount of image noise.

BRIEF DESCRIPTION OF DRAWINGS

FIG. 4(a) is a schematic diagram for explaining a streak artifact 50b generated in a lower limb sectional view 50, and FIG. 4(b) is a diagram for explaining a region 65 where high absorbers cross each other on projection data.

FIG. 16 is a diagram for explaining the feature amount C1.

FIG. 17 is a diagram for explaining the feature amount C2.

FIG. 31 is a flowchart showing the procedure of processing for calculating the streak reduction rate Str from projection data.

DESCRIPTION OF EMBODIMENTS

Figure 1:
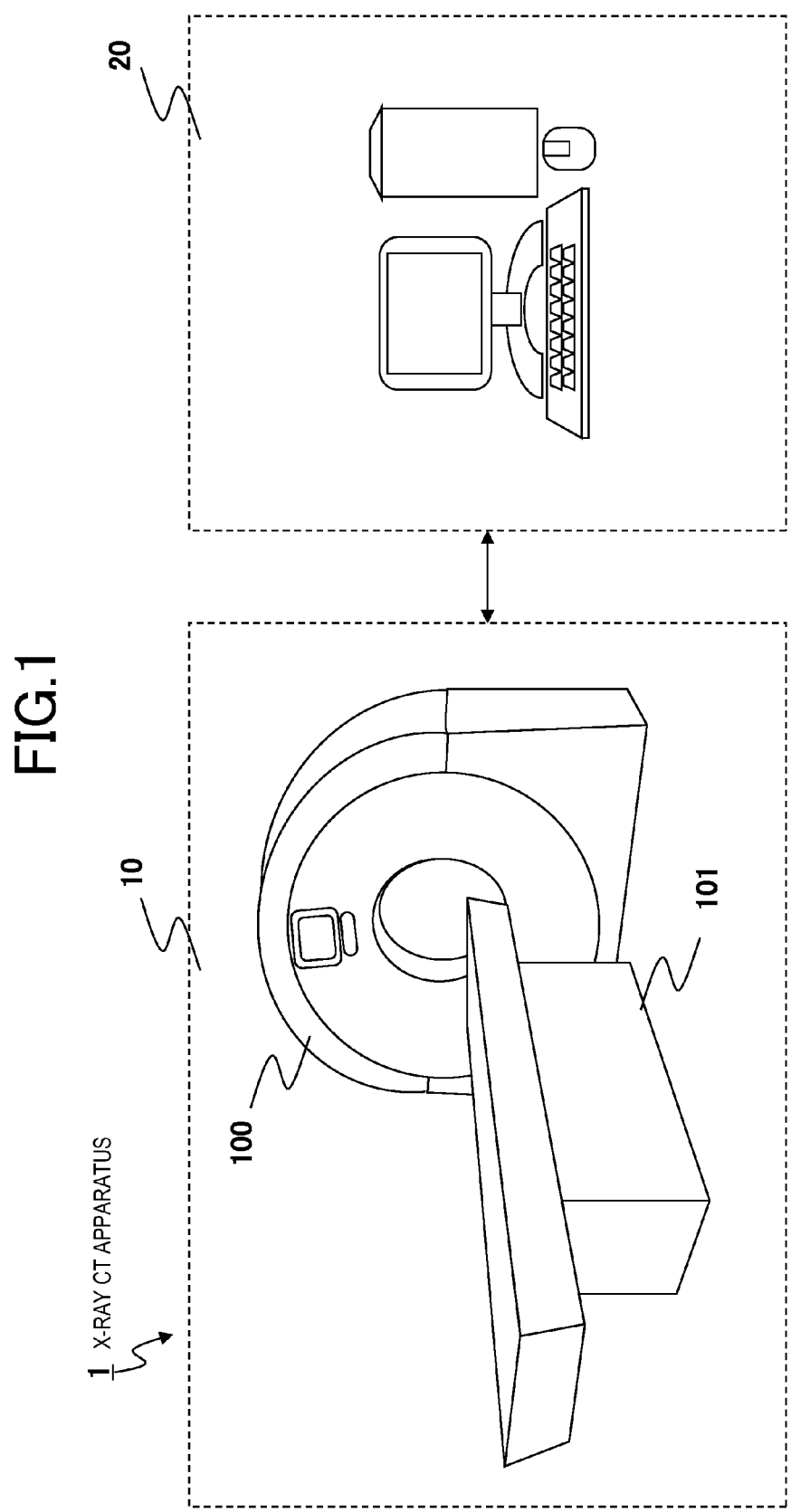
FIG. 1 is an external view showing the overall configuration of an X-ray CT apparatus 1.

Hereinafter, preferred embodiments of the present invention will be described in detail with reference to the diagrams. First, the hardware configuration of an X-ray CT apparatus 1 will be described with reference to FIGS. 1 and 2.

The X-ray CT apparatus 1 is configured to mainly include a scanner 10 and an operation unit 20.

The scanner 10 includes a gantry 100, a bed device 101, an X-ray generator 102, an X-ray detector 103, a collimator device 104, a high voltage generator 105, a data acquisition system 106, a driving device 107, and the like. The operation unit 20 includes a central controller 200, an input and output device 201, an arithmetic device 202, and the like.

The operator inputs scanning conditions, reconstruction conditions, or the like through the input and output device 201. Examples of the scanning conditions include an X-ray beam width, bed movement speed, tube current, tube voltage, scanning range (body axis direction range), the number of scanning views per rotations, and the like. In addition, examples of the reconstruction conditions include a region of interest, field of view (FOV), a reconstruction filter function, and the like. The input and output device 201 includes a display device 211 to display a CT image and the like, an input device 212, such as a mouse, a trackball, a keyboard, and a touch panel, a storage device 213 to store data, and the like.

The central controller 200 receives an input of scanning conditions or reconstruction conditions, and transmits a control signal required for scanning to each device included in the scanner 10. The collimator device 104 controls the position of the collimator based on the control signal. When scanning is started in response to the scanning start signal, the high voltage generator 105 applies a tube voltage and a tube current to the X-ray generator 102 based on the control signal. In the X-ray generator 102, electrons of energy corresponding to the applied tube voltage are emitted from the cathode, and the emitted electrons collide with a target (anode). As a result, X-rays of energy corresponding to the electron energy are emitted to an object 3.

The driving device 107 rotates the X-ray generator 102, the X-ray detector 103, and the like around the object 3 based on the control signal. The bed device 101 controls a bed based on the control signal.

The irradiation region of X-rays emitted from the X-ray generator 102 is limited by the collimator. X-rays are absorbed (attenuated) into each tissue in the object 3 according to the X-ray attenuation coefficient, are transmitted through the object 3, and are detected by the X-ray detector 103 disposed at a position facing the X-ray generator 102. The X-ray detector 103 is formed by a plurality of detection elements disposed in a two-dimensional direction (a channel direction and a column direction perpendicular to the channel direction). X-rays received by each detection element are converted into actual projection data. That is, X-rays detected by the X-ray detector 103 are acquired as projection data after various kinds of data processing (change to digital data, LOG conversion, calibration, and the like) are performed by the data acquisition system 106, and are input to the arithmetic device 202.

In this case, since the X-ray generator 102 and the X-ray detector 103 facing each other rotate around the object 3, the X-ray generator 102 emits X-rays from the periphery of the object 3. The X-ray detector 103 detects X-rays transmitted through the object 3. The acquisition unit of projection data is a "view".

The arithmetic device 202 is configured to include a reconstruction arithmetic device 221, an image processing device 222, and the like.

The reconstruction arithmetic device 221 receives an input of projection data acquired by the data acquisition system 106. The reconstruction arithmetic device 221 creates corrected projection data by performing successive approximation projection data correction processing (hereinafter, also referred to as iterative processing) on the projection data. Then, a CT image is reconstructed using the corrected projection data.

The reconstruction arithmetic device 221 may create projection data by reading the measurement data that is stored in the storage device 213 or a recording medium after being acquired by scanning, and may perform the successive approximation projection data correction processing described above or may perform CT image reconstruction processing.

The present invention relates to the improvement of successive approximation projection data correction processing (iterative processing). The details of the processing according to the present invention will be described later.

The reconstruction arithmetic device 221 stores the generated CT image in the storage device 213. In addition, the reconstruction arithmetic device 221 displays the generated CT image on the display device 211. Alternatively, the image processing device 222 performs image processing on the CT image stored in the storage device 213, and displays an image after the image processing on the display device 211.

Types of the X-ray CT apparatus 1 are largely divided into a multi-slice CT, which uses the X-ray detector 103 in which detection elements are arrayed in two-dimensional directions, and a single-slice CT, which uses the X-ray detector 103 in which detection elements are arrayed in a row, that is, in a one-dimensional direction (only in the channel direction). In the multi-slice CT, X-ray beams spreading in a conical shape or in a pyramid shape are emitted from the X-ray generator 102, which is an X-ray source, according to the X-ray detector 103. In the single-slice CT, X-ray beams spreading in a fan shape are emitted from the X-ray generator 102. Typically, in the scanning of the X-ray CT apparatus 1, X-rays are emitted while the X-ray generator 102 is rotating around the object 3 placed on the bed (however, positioning scanning is excluded).

A scanning mode in which the bed is fixed during scanning and the X-ray generator 102 rotates around the object 3 in the shape of a circular orbit is called an axial scan or the like. A scanning mode in which the bed moves continuously and the X-ray generator 102 rotates around the object 3 in the shape of a spiral orbit is called a spiral scan or the like.

In the case of a step-and-shoot scan, the bed device 101 maintains the bed in a stationary state during the scanning. In the case of a spiral scan, the bed device 101 moves the bed in parallel to the body axis direction of the object 3 during the scanning according to the bed movement speed that is one of the scanning conditions.

Figure 3:
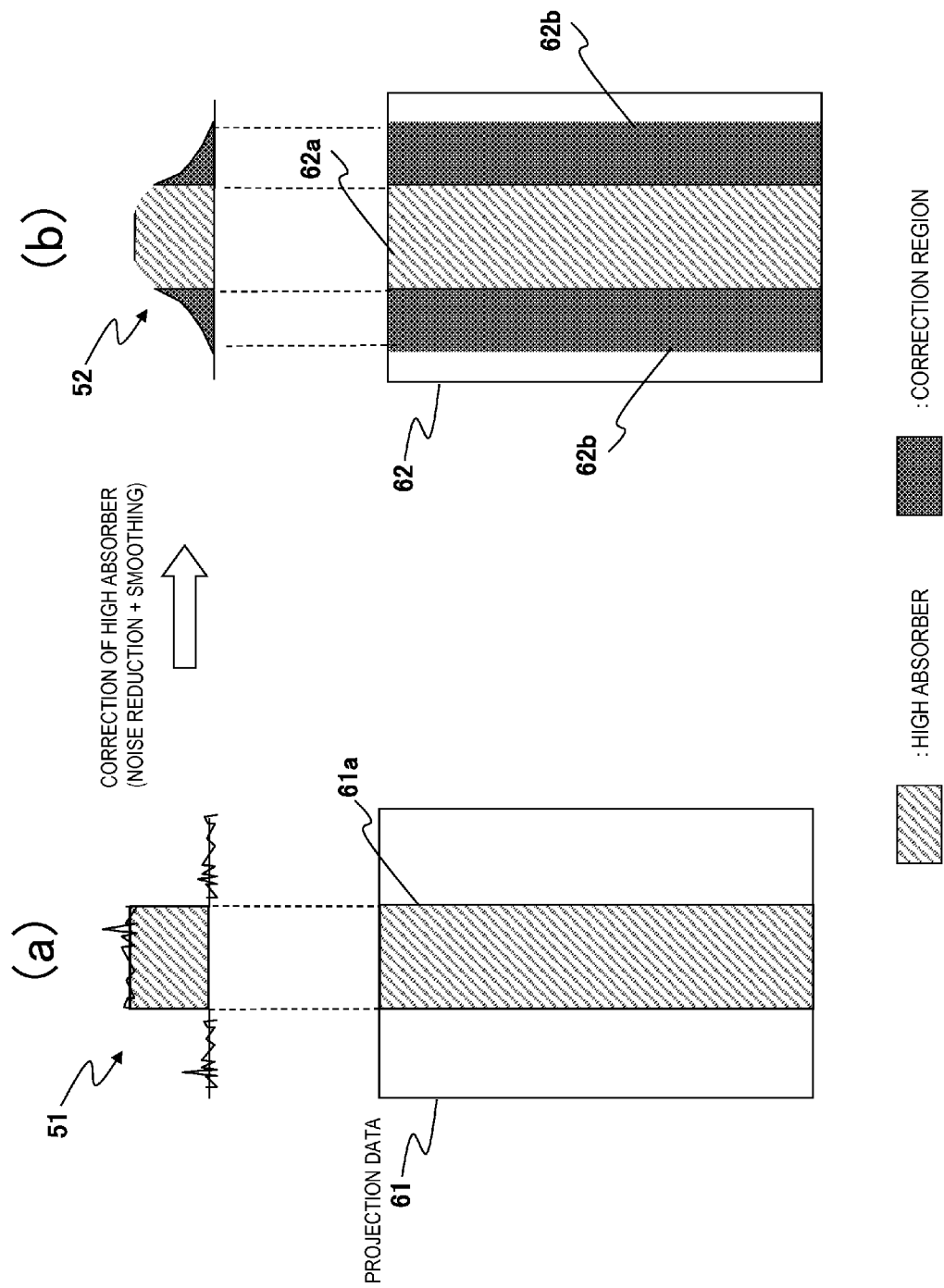
FIG. 3 is a diagram for explaining a change in projection data due to noise reduction processing f1.

Next, noise included in projection data will be described with reference to FIGS. 3 and 4.

FIG. 3(a) is a diagram schematically showing projection data 61 and its profile 51 obtained when scanning a high absorber. FIG. 3(b) is a diagram schematically showing corrected projection data 62 and its profile 52 after performing conventional successive approximation projection data correction processing (noise reduction processing f1). Shaded portions 61a and 62a included in the projection data 61 and 62 are projection data corresponding to a high absorber.

Shaded portions 161a and 62a included in the projection data 61 and 62 are projection data corresponding to a high absorber.

Equation (1) shows the update equation of the conventional successive approximation projection data correction processing.

$$p_i^{(n)} = F(p_i^{(n-1)}, y_i, \beta, d_i), p_i^{(0)} = y_i \qquad (1)$$

In Equation (1) described above, F is an update function, p is an update projection value, y is an original projection value, $\beta$ is a correction coefficient (smoothing coefficient), d is a detection characteristic value, i is a detection element number, and n is the number of iterations.

In addition, an equation corresponding to Equation (1) described above is described in NPL 1. Equation (1) is an equation corresponding to Equation (11) described in p. 1274 of NPL 1. In this specification, in order to give explanation along the spirit of the present invention, each equation is described in different format and symbols from NPL 1. However, the content of Equation (1) described above is the same as the content of each equation described in NPL 1.

When trying to obtain a high noise reduction effect by performing the noise reduction processing f1 using a conventional method, as shown in FIG. 3(b), a region 62b of so-called "smoothing" where the edge of a high signal portion is smooth is generated. If an image is reconstructed using projection data when such a phenomenon occurs, for example, streak artifacts may be generated around a high absorber, such as a bone.

FIG. 4(a) is a schematic diagram of an image 50 obtained by reconstructing projection data in which "smoothing" is caused by the noise reduction processing f1. FIG. 4(b) is difference data 63 of the projection data before and after the noise reduction processing f1. The image 50 shows a tomographic image of the lower limb. Streak artifacts 50b are generated around a bone 50a that is a high absorber, and appear as a shadow that is not present in the original image. In particular, in a part where a plurality of high absorbers are present, such as a lower limb or a shoulder, as shown in FIG. 4(b), over-correction occurs in a region 65 where the high absorbers cross each other on the difference data 63. In this case, artifacts are easily generated.

Therefore, the reconstruction arithmetic device 221 of the X-ray CT apparatus 1 according to the present invention corrects projection data by combining the noise reduction processing f1 for adjusting the amount of noise in the image (first processing function) and signal strength maintenance processing f2 for adjusting the amount of streaks (second processing function) in an appropriate ratio. For this reason, in the reconstruction arithmetic device 221, adjustment processing f3 for adjusting the application ratio of two processes having different characteristics (noise reduction processing f1 and signal strength maintenance processing f2) is introduced.

The application ratio of the noise reduction processing f1 and the signal strength maintenance processing f2 in the adjustment processing f3 can be adjusted by an adjustment coefficient $\alpha$ depending on the requested image quality. When performing the signal strength maintenance processing f2, if the iterative processing is performed using the original correction coefficient $\beta$, the noise reduction effect is reduced in general. For this reason, the value of the correction coefficient $\beta$ is also updated. In the following explanation, a combination of the adjustment coefficient $\alpha$ and the correction coefficient $\beta$ is called a calibration coefficient. The reconstruction arithmetic device 221 creates corrected projection data by repeatedly performing the adjustment processing f3, which includes the noise reduction processing f1 and the signal strength maintenance processing f2 for adjusting the amount of streaks, based on the calibration coefficient ($\alpha$, $\beta$).

Specifically, the reconstruction arithmetic device 221 of the present invention performs projection data correction processing by applying the following iterative equations (2), (3), and (4) to the projection data.

$$p_{F\_i}^{(n)} = F(p_{F\_i}^{(n-1)}, y_i, \beta', d_i) \quad (2)$$

$$p_{G\_i}^{(n)} = G(p_{G\_i}^{(n-1)}, y_i, \beta', d_i) \quad (3)$$

$$p_i^{(n)} = \alpha \cdot p_{F\_i}^{(n)} + (1-\alpha) \cdot p_{G\_i}^{(n)} \quad (4)$$

Equation (2) is the iterative equation f1 of the noise reduction processing, Equation (3) is the iterative equation f2 of the signal strength maintenance processing, and Equation (4) is the adjustment processing f3 for adjusting the application ratio of the noise reduction processing f1 and the signal strength maintenance processing f2. In Equations (2), (3), and (4) described above, F and G are update functions, p is an update projection value, y is an original projection value, $\beta$ and $\beta'$ are correction coefficients, d is a detection characteristic value, i is a detection element number, n is the number of iterations, and $\alpha$ is an adjustment coefficient.

More specifically, as the noise reduction processing function, for example, the following evaluation function (5) and iterative equation (6) may be used. The evaluation function is derived using a solution called a Ridge type (secondary type penalty term), and the iterative equation is derived using a solution called a Gauss-Seidel method (reference: NPL 2).

$$\Phi(p) = \sum_i d_i(y_i - p_i)^2 + \beta \sum_i \sum_{m \in N_i} w_{im}(p_i - p_m)^2 \quad (5)$$

$$p_i^{(n+1)} = \frac{y_i + \frac{\beta}{d_i}\left(\sum_{m \in N_i^1} w_{im} p_m^{(n+1)} + \sum_{m \in N_i^2} w_{im} p_m^{(n)}\right)}{1 + \frac{\beta}{d_i}\sum_{m \in N_i} w_{im}} \quad (6)$$

As the signal strength maintenance processing function, for example, the following evaluation function (7) and iterative equation (8) may be used. The evaluation function is derived using a solution called a Lasso type (total variation (TV) type penalty term), and the iterative equation is derived using a solution called an iterative soft-thresholding algorithm (ISTA) (reference: NPL 3).

$$\Phi(p) = \sum_i d_i(y_i - p_i)^2 + \beta \sum_i \sum_{m \in N_i} w_{im}|p_i - p_m| \quad (7)$$

$$\begin{aligned} p_i^{(n+1)} &= y_i - \sum_{m \in N_i} w_{mi}(z_i^{(n)} - z_m^{(n)}) \\ x_i^{(n+1)} &= z_i^{(n)} + \sum_{m \in N_i} w_{im}(p_i^{(n+1)} - p_m^{(n+1)}) \\ z_i^{(n+1)} &= \begin{cases} \beta/2d_i & |x_i^{(n+1)}| > \beta/2d_i \\ x_i^{(n+1)} & |x_i^{(n+1)}| \le \beta/2d_i \end{cases} \end{aligned} \quad (8)$$

In addition, the evaluation functions and the iterative equations described above are examples, and are not limited thereto.

Figure 5:
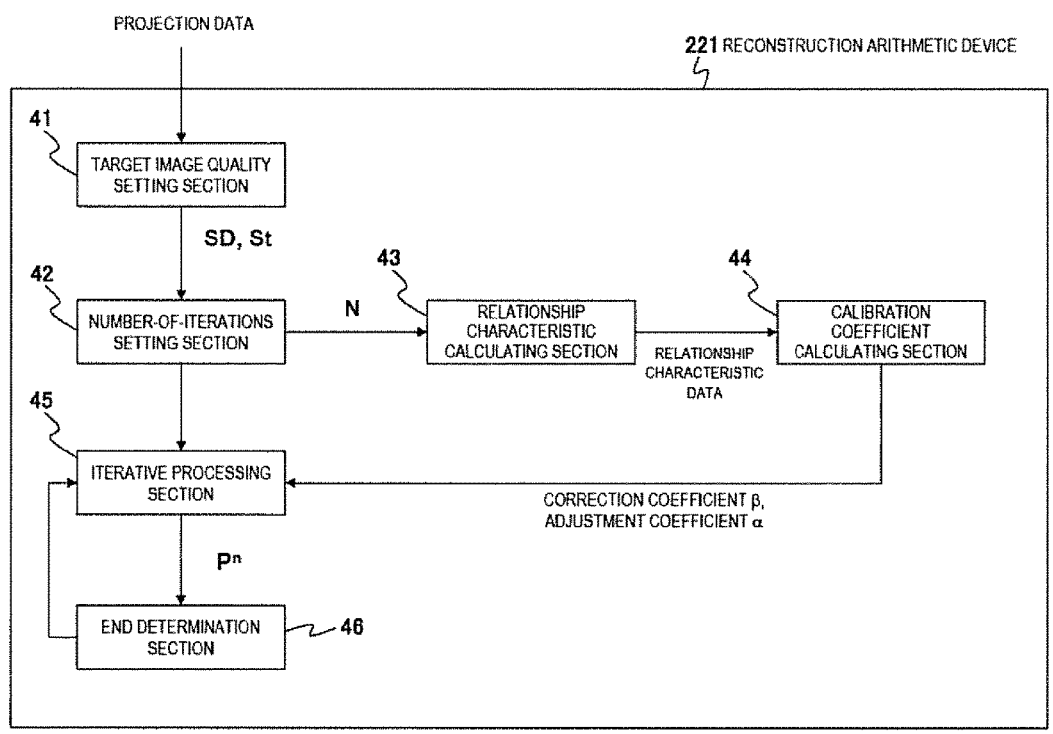
FIG. 5 is a functional block diagram of a reconstruction arithmetic device 221.

The functional configuration of the X-ray CT apparatus 1 of the present invention will be described with reference to FIG. 5. In particular, FIG. 5 shows the functional configuration of the reconstruction arithmetic device 221.

The reconstruction arithmetic device 221 of the X-ray CT apparatus 1 according to the present invention mainly includes a target image quality setting section 41, a number-of-iterations setting section 42, a relationship characteristic calculating section 43, a calibration coefficient calculating section 44, an iterative processing section 45, and an end determination section 46.

The target image quality setting section 41 sets a target image quality that is the image quality obtained after the correction of projection data. Parameters used as the target image quality are an image SD value or a noise reduction rate r, which is an indicator regarding the amount of noise included in the image (first image quality parameter), and a streak amount St or a streak reduction rate Str, which is an indicator regarding streak artifacts (second image quality parameter).

The image SD value and the noise reduction rate r are first image quality parameters adjusted mainly by the noise reduction processing f1 described above. The streak amount St or the streak reduction rate Str are second image quality parameters adjusted mainly by the signal strength maintenance processing f2 described above.

As will be described later, the reconstruction arithmetic device 221 determines the calibration coefficient ($\alpha$, $\beta$) used in iterative equations (2) to (4) based on relationship characteristic data 8 showing the relationship between the noise reduction rate r and the streak reduction rate Str (refer to FIG. 6). Therefore, the target image quality setting section 41 calculates the value of each parameter (the noise reduction rate r and the streak reduction rate Str) based on the desired target image quality set by the operator, for example. The noise reduction rate r is a ratio of the SD value of the original image reconstructed from projection data before applying the noise reduction processing f1 and the SD value (target SD value) of a corrected image reconstructed from projection data after applying the noise reduction processing f1. The streak reduction rate Str is a ratio of the amount of streaks of a corrected image obtained by reconstructing projection data after applying the noise reduction processing f1 and the amount of streaks (target St) of an image obtained after applying calibration processing to be described later.

The number-of-iterations setting section 42 sets the number of iterations of the successive approximation projection data correction processing (iterative processing) for correcting the projection data.

The relationship characteristic calculating section 43 creates the relationship characteristic data 8 indicating the relationship between the first and second image quality parameters (the noise reduction rate r and the streak reduction rate Str) and calibration coefficients (the adjustment coefficient α and the correction coefficient β) of the iterative processing. The relationship characteristic data 8 is calculated based on projection data as a reference, such as projection data measured using a phantom or the like.

Figure 6:
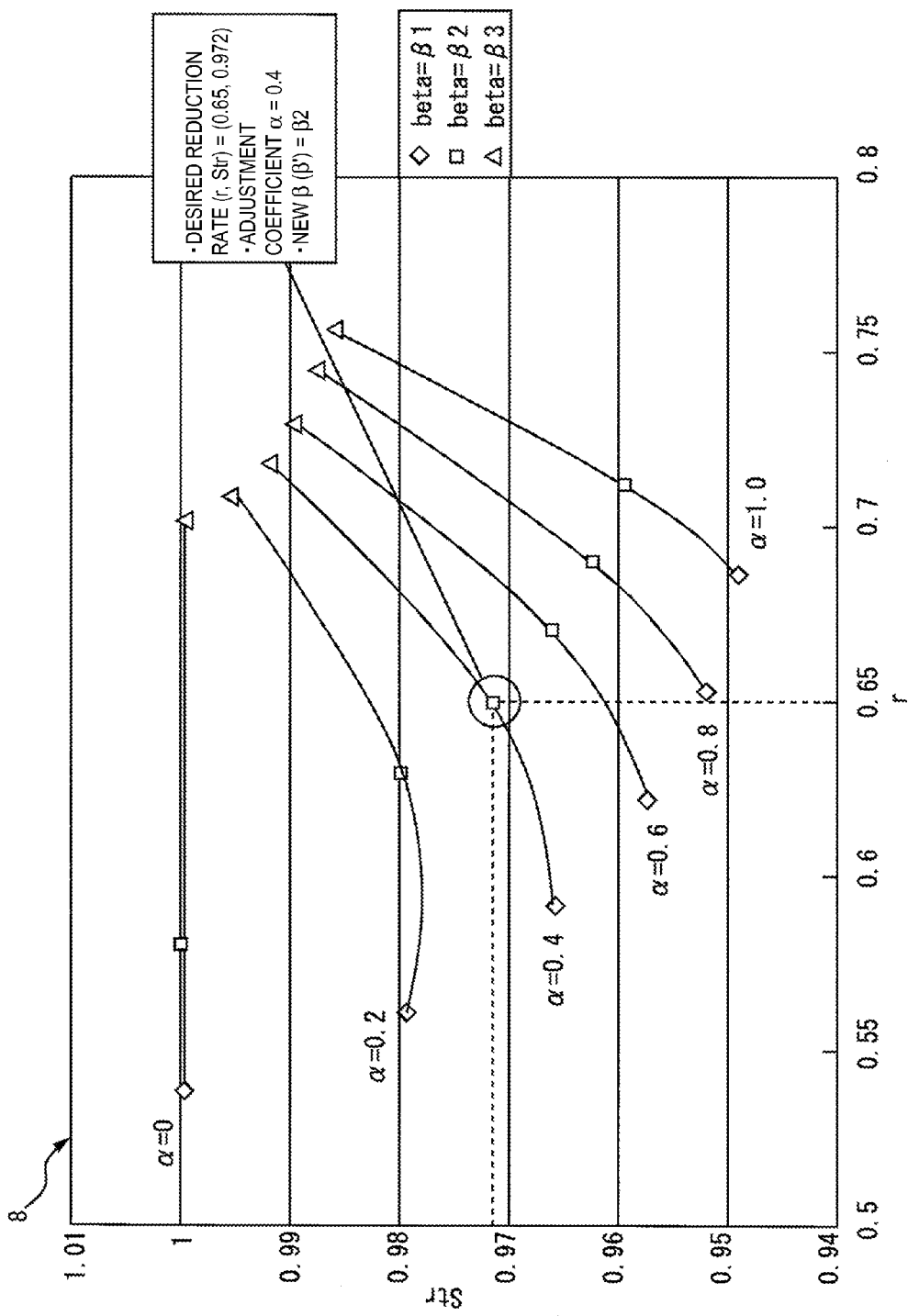
FIG. 6 is an example of relationship characteristic data 8.

FIG. 6 shows an example of the relationship characteristic data 8. The relationship characteristic data 8 shown in FIG. 6 is an r-Str graph showing the relationship between the adjustment coefficient α and the correction coefficient β with the noise reduction rate r on the horizontal axis and the streak reduction rate Str on the vertical axis.

For example, when the adjustment coefficient α=0.4 and the correction coefficient β=β2 are set to execute the successive approximation projection data correction processing, the noise reduction rate r=0.65 and the streak reduction rate Str=0.972 are obtained. The method of creating the relationship characteristic data 8 will be described later.

In addition, the notation "β'" in FIG. 6 is a new correction coefficient that is updated when introducing the adjustment coefficient α. When the signal strength maintenance processing f2 is performed with the correction coefficient β that is used when performing only the noise reduction processing f1, the noise reduction effect is weakened in general. Therefore, the new correction coefficient β' is applied by updating the correction coefficient β so that the same effect as the original noise reduction effect can be obtained.

The calibration coefficient calculating section 44 calculates calibration coefficients (the adjustment coefficient α and the correction coefficient β) which are applied to projection data to be corrected, based on the relationship characteristic data 8 and the set target image quality (the noise reduction rate r and the streak reduction rate Str or the image SD value and the streak amount St).

When the relationship characteristic data 8 is stored as r-Str data, the calibration coefficient (α, β) is calculated based on the following relational equation (9).

$$(\alpha, \beta) = \Omega(r, Str) \quad (9)$$

Similarly, when the relationship characteristic data is stored as SD-St data, the calibration coefficient (α, β) is calculated based on the following relational equation (10).

$$(\alpha, \beta) = \Omega'(SD, St) \quad (10)$$

The iterative processing section 45 creates corrected projection data by performing the iterative processing (adjustment processing f3), which includes the noise reduction processing f1 and the signal strength maintenance processing f2, based on the number of iterations set by the number-of-iterations setting section 42 and the calibration coefficient (α, β) calculated by the calibration coefficient calculating section 44.

The end determination section 46 determines whether or not to repeat the iterative processing by the number of iterations. When the number of iterations has not ended, the iterative processing of the iterative processing section 45 is repeated. When the number of iterations has ended, corrected projection data obtained after applying the iterative processing is output.

The reconstruction arithmetic device 221 reconstructs a CT image based on the corrected projection data. The display device 211 displays the CT image reconstructed by the reconstruction arithmetic device 221.

Next, relationship characteristic calculation processing for creating the relationship characteristic data 8 will be described with reference to FIGS. 7 to 9. The relationship characteristic calculation processing is processing for creating the relationship characteristic data 8 shown in FIG. 6.

Figure 7:
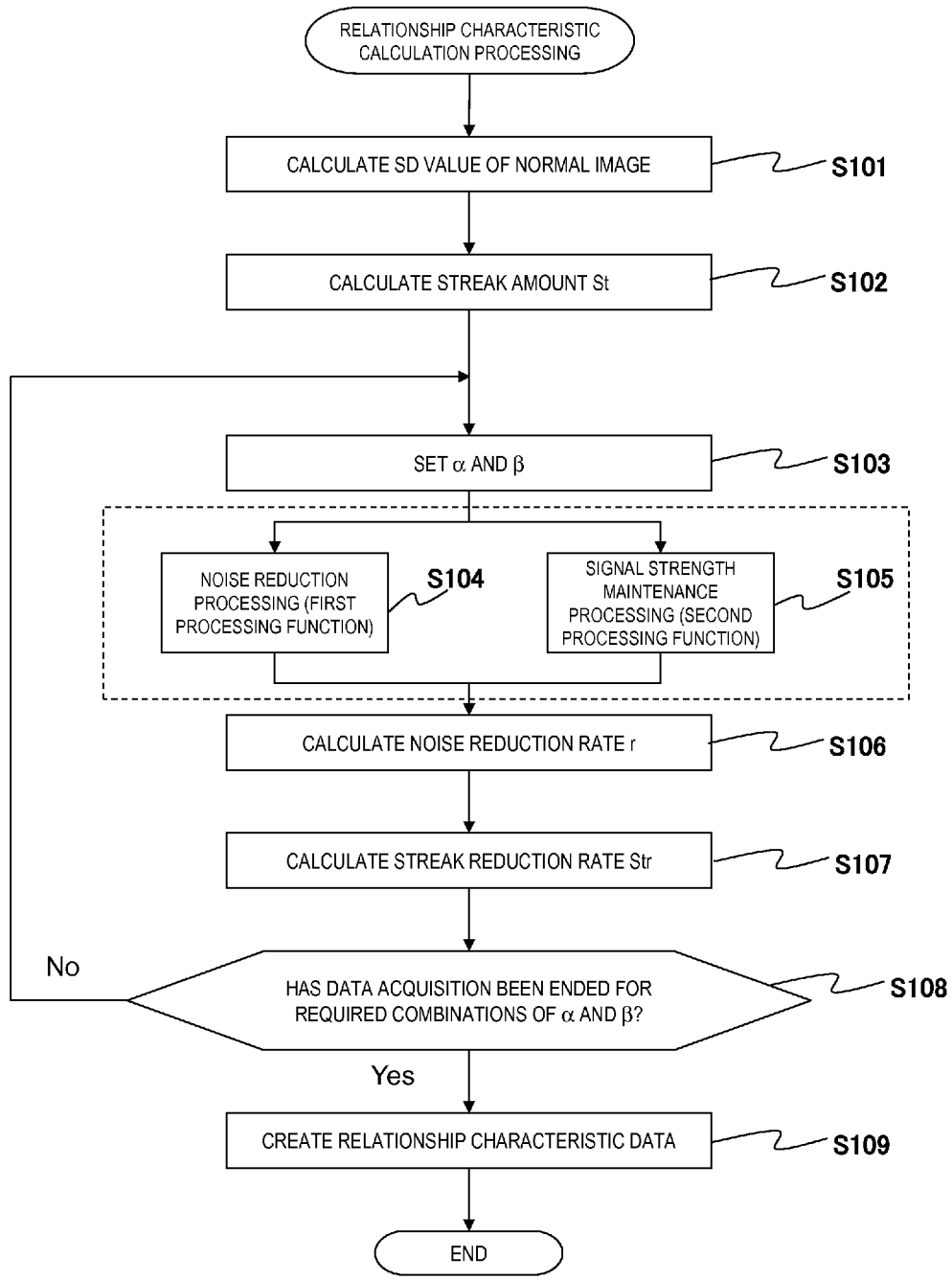
FIG. 7 is a flowchart for explaining the procedure of relationship characteristic calculation processing performed by the reconstruction arithmetic device 221.
Figure 8:
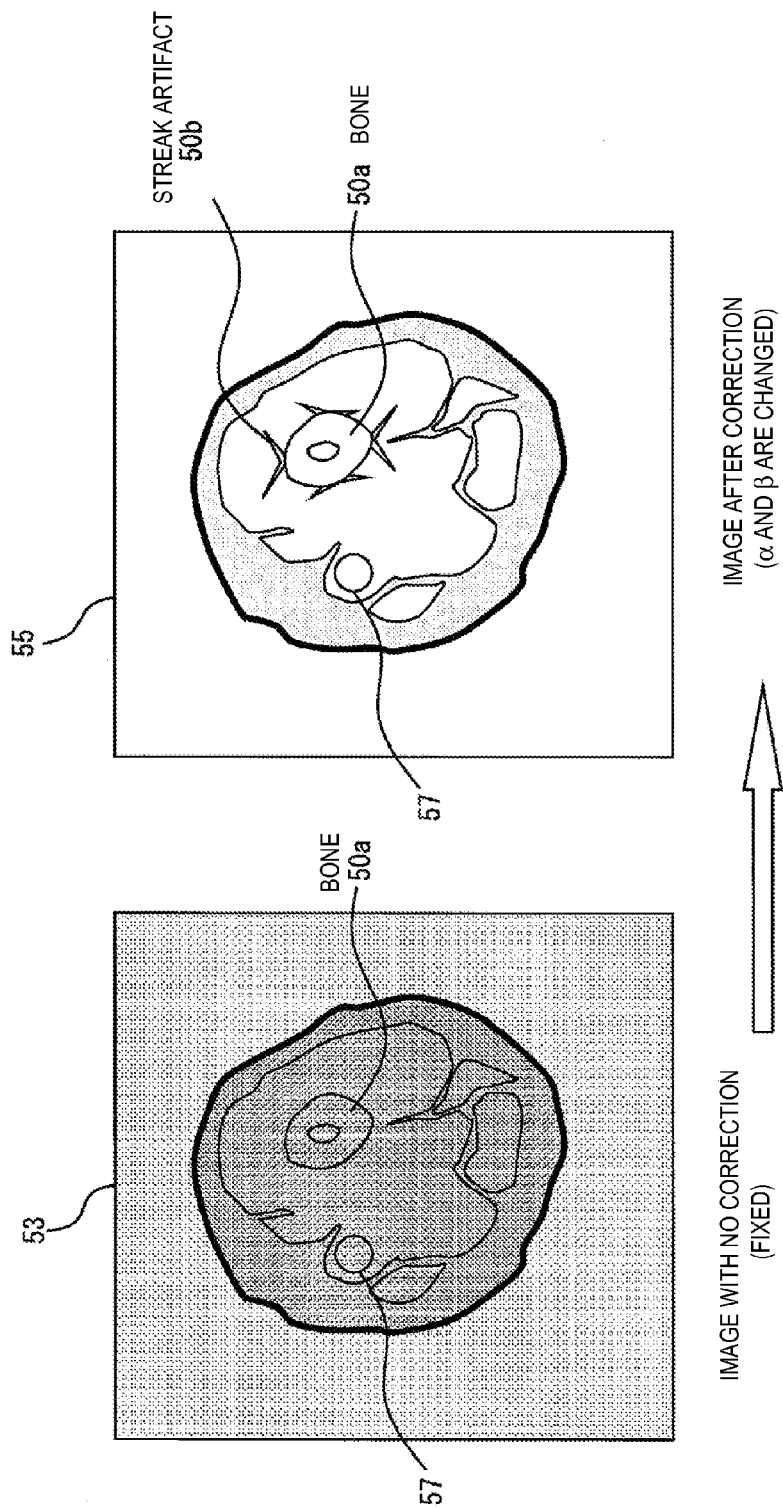
FIG. 8 is a diagram for explaining a method of calculating a noise reduction rate r.

As shown in FIG. 7, the reconstruction arithmetic device 221 (relationship characteristic calculating section 43) reconstructs an image (normal image 53 in FIG. 8) based on the projection data measured in advance using a phantom or the like. Then, an image SD value of the normal image 53 is calculated (step S101). The SD value is an SD value in an ROI 57 that is set at an arbitrary position of the normal image 53, as shown in FIG. 8.

In addition, the reconstruction arithmetic device 221 reconstructs the projection data after performing the noise reduction processing f1 by applying the arbitrary correction coefficient β, and calculates the streak amount St of an obtained image 54 (step S102). The streak amount St is the streak amount St of an ROI 58 set on the streak of the image 54 obtained by reconstructing the projection data after the noise reduction processing f1, as shown in FIG. 9.

Then, the reconstruction arithmetic device 221 sets an arbitrary calibration coefficient (α, β) (step S103), and performs the noise reduction processing f1 on initial projection data Raw_0, thereby obtaining projection data Raw_A. Similarly, the reconstruction arithmetic device 221 performs the signal strength maintenance processing f2 on the initial projection data Raw_0, thereby obtaining projection data Raw_B. In addition, the reconstruction arithmetic device 221 performs the adjustment processing f3 using the adjustment coefficient α, thereby obtaining corrected projection data Raw_C from Raw_A and Raw_B. With the Raw_C as new input data of f1 and f2, this is repeatedly performed by only the number of iterations set in advance (steps S104 and S105). Thus, the corrected projection data Raw_C on the set calibration coefficient (α, β) is calculated. Then, the reconstruction arithmetic device 221 reconstructs a corrected image 55 based on the corrected projection data Raw_C. The reconstruction arithmetic device 221 sets an ROI 57 at the same position as the ROI 57, which is set in step S101, on the corrected image 55 as shown in FIG. 8, and calculates the SD value of the corrected image 55. The noise reduction rate r in the ROI 57 is calculated from the ratio of the SD value obtained herein and the SD value obtained in step S101 (step S106).

Figure 9:
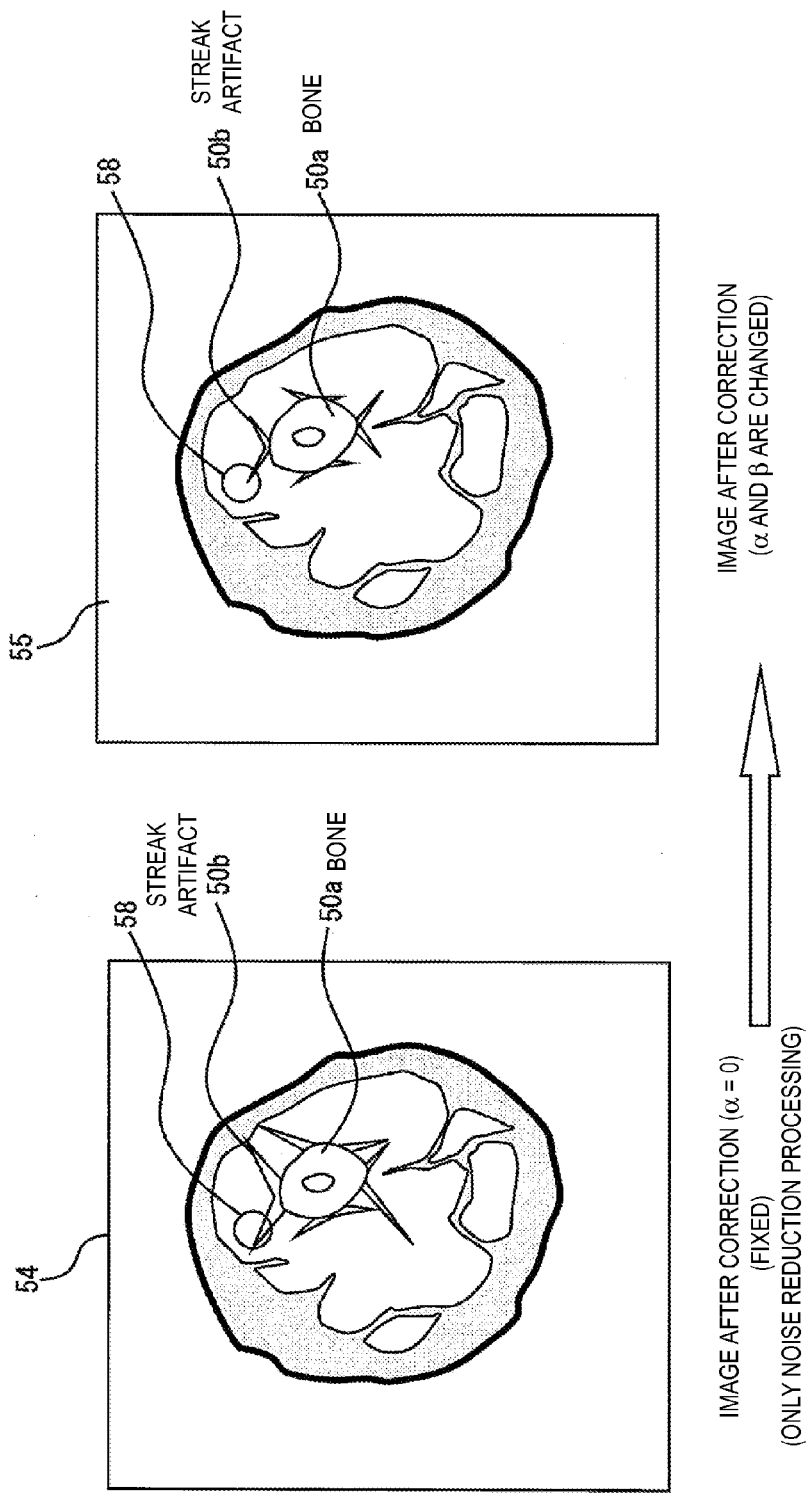
FIG. 9 is a diagram for explaining a method of calculating a streak reduction rate Str.

The reconstruction arithmetic device 221 sets an ROI 58 at the same position as the ROI 58, which is set in step S102, on the corrected image 55 reconstructed based on the corrected projection data Raw_C as shown in FIG. 9, and calculates the streak amount St in the ROI 58. The streak reduction rate Str in the ROI 58 is calculated from the ratio of the streak amount St obtained herein and the streak amount St obtained in step S102 (step S107).

The reconstruction arithmetic device 221 repeats the iterative processing and the calculation of the noise reduction rate r and the streak reduction rate Str while changing the calibration coefficient (α, β) by an arbitrary unit width until a desired range is covered (step S108; No→steps S103 to S107). When the desired range is covered, the reconstruction arithmetic device 221 creates the relationship characteristic data 8 by associating the noise reduction rate r and the streak reduction rate Str obtained by the processing in steps S103 to S108 with the calibration coefficient (α, β), and stores the relationship characteristic data 8 in the storage device 213 (step S109).

The relationship characteristic data 8 shown in FIG. 6 is obtained by changing β to β1, β2, and β3 and changing α in units of 0.2 from 0 to 1.

Figure 13:
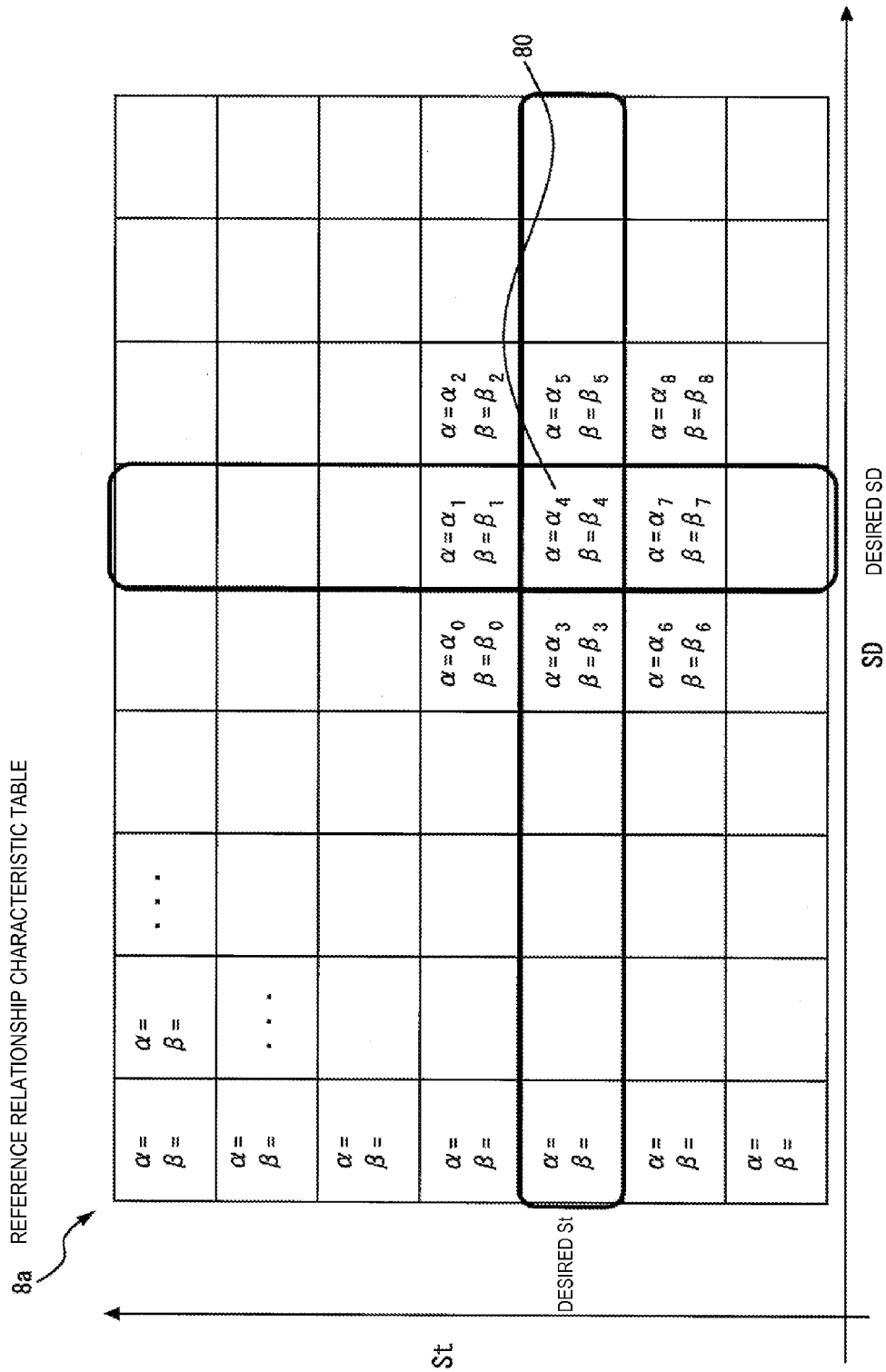
FIG. 13 is an example of a reference relationship characteristic table 8a in the form of a look-up table.

Although the relationship characteristic data 8 may be stored as r-Str data showing the relationship between the noise reduction rate r and the streak reduction rate Str and the calibration coefficient (α, β) as shown in FIG. 6, the relationship characteristic data 8 may also be stored as SD-St data showing the relationship between the image SD value and the streak amount St and the calibration coefficient (α, β) (refer to FIG. 13). In any case, the relationship characteristic data 8 shows the relationship between two image quality parameters (the first image quality parameter that is an indicator regarding noise and the second image quality parameter that is an indicator regarding the streak) having different characteristics and the calibration coefficient (α, β).

In addition, the relationship characteristic data 8 may be stored in the form of a graph as shown in FIG. 6, or may be stored in the form of a look-up table as shown in FIG. 13. In addition, the relationship characteristic data 8 may be stored in the form of an approximation function as described in a second embodiment. In addition, the relationship characteristic data 8 may be created and stored for each of the scanning conditions or each scanning part. In this specification, relationship characteristic data in the form of a look-up table will be described in the first embodiment. Relationship characteristic data in the form of an approximation function will be described in the second embodiment. Relationship characteristic data for each of the scanning conditions will be described in a third embodiment.

Figure 10:
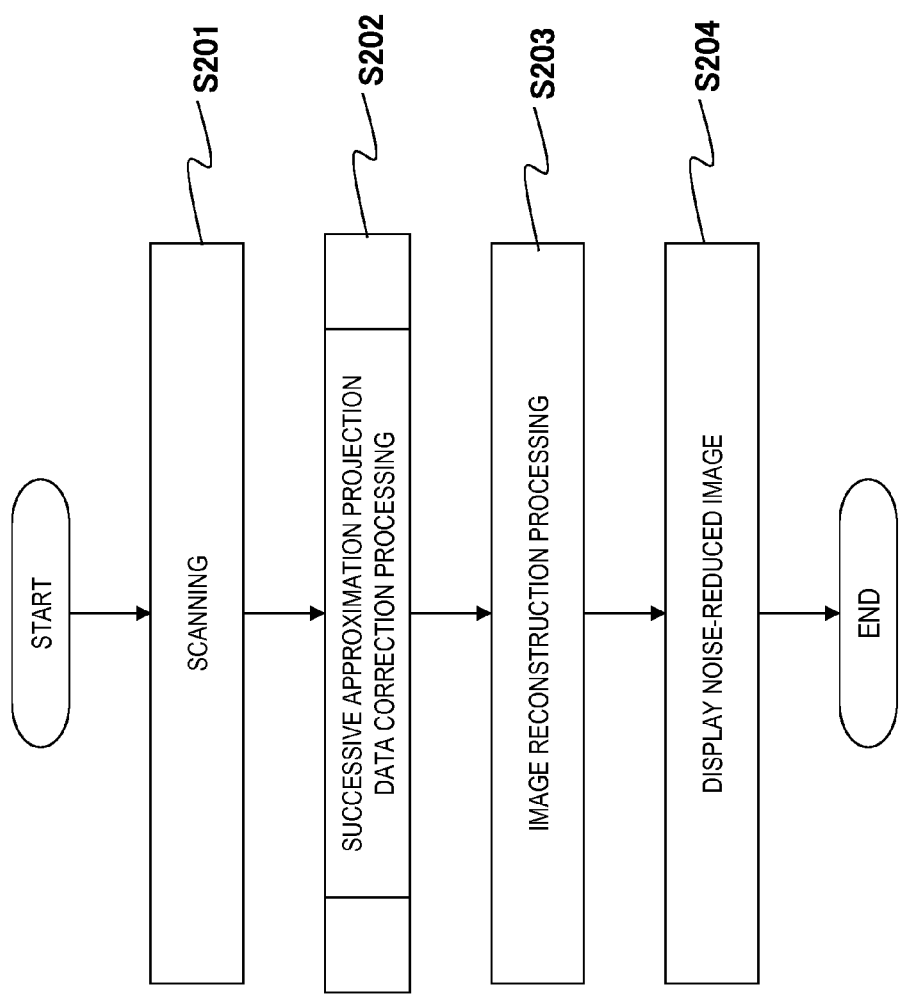
FIG. 10 is a flowchart showing the flow of overall processing.

Next, the flow of the entire process of the X-ray CT apparatus 1 of the present invention will be described with reference to FIG. 10.

First, the X-ray CT apparatus 1 performs positioning scanning for the object 3. Then, the X-ray CT apparatus sets various conditions, such as scanning conditions or reconstruction conditions, based on a positioning image captured by the positioning scanning. Then, the X-ray CT apparatus 1 performs tomography (main scanning), thereby acquiring projection data (step S201).

The reconstruction arithmetic device 221 performs successive approximation projection data correction processing on the acquired projection data (step S202). In the present invention, as an iterative operation of the successive approximation projection data correction processing, the reconstruction arithmetic device 221 performs the iterative processing f3 including the noise reduction processing f1 and the streak amount reduction processing (signal strength maintenance processing f2).

The reconstruction arithmetic device 221 generates a CT image by performing image reconstruction using the corrected projection data that has been corrected by the successive approximation projection data correction processing (step S203).

The reconstruction arithmetic device 221 displays the generated CT image on the display device 211 (step S204).

The successive approximation projection data correction processing in step S202 will be described with reference to FIG. 11.

First, the reconstruction arithmetic device 221 acquires projection data from the data acquisition system 106 (step S301). In step S301, projection data that has been measured in advance and stored in the storage device 213 or the like may be acquired.

Then, the reconstruction arithmetic device 221 determines a target image quality (the image SD value and the streak amount St, or the noise reduction rate r and the streak reduction rate Str) (step S302). As the target value of the image quality (the image SD value and the streak amount St, or the noise reduction rate r and the streak reduction rate Str), for example, a value input through the input device 212 is used. When the relationship characteristic data used in the calibration coefficient calculation processing to be described later is stored as r-Str data, the reconstruction arithmetic device 221 calculates the noise reduction rate r and the streak reduction rate Str corresponding to input target image qualities SD and St. Conversely, when the relationship characteristic data is stored as SD-St data, the image SD value and the streak amount St corresponding to input target image qualities r and Str are calculated.

In addition, the reconstruction arithmetic device 221 sets the number of iterations of the iterative processing (step S303).

Then, the reconstruction arithmetic device 221 calculates the calibration coefficient (α, β) corresponding to the target image quality parameters r and Str determined in step S302 (step S304). When the relationship characteristic data is stored as r-Str data, the calibration coefficient is calculated based on the following relational equation (9) as described above.

$$(\alpha, \beta) = \Omega(r, Str) \quad (9)$$

Similarly, when the relationship characteristic data is stored as SD-St data, the calibration coefficient is calculated based on the following relational equation (10).

$$(\alpha, \beta) = \Omega'(SD, St) \quad (10)$$

For example, the reconstruction arithmetic device 221 calculates a combination of the calibration coefficient (α, β) corresponding to the parameters r and Str set as target image qualities with reference to the relationship characteristic data 8 shown in FIG. 6.

Figure 12:
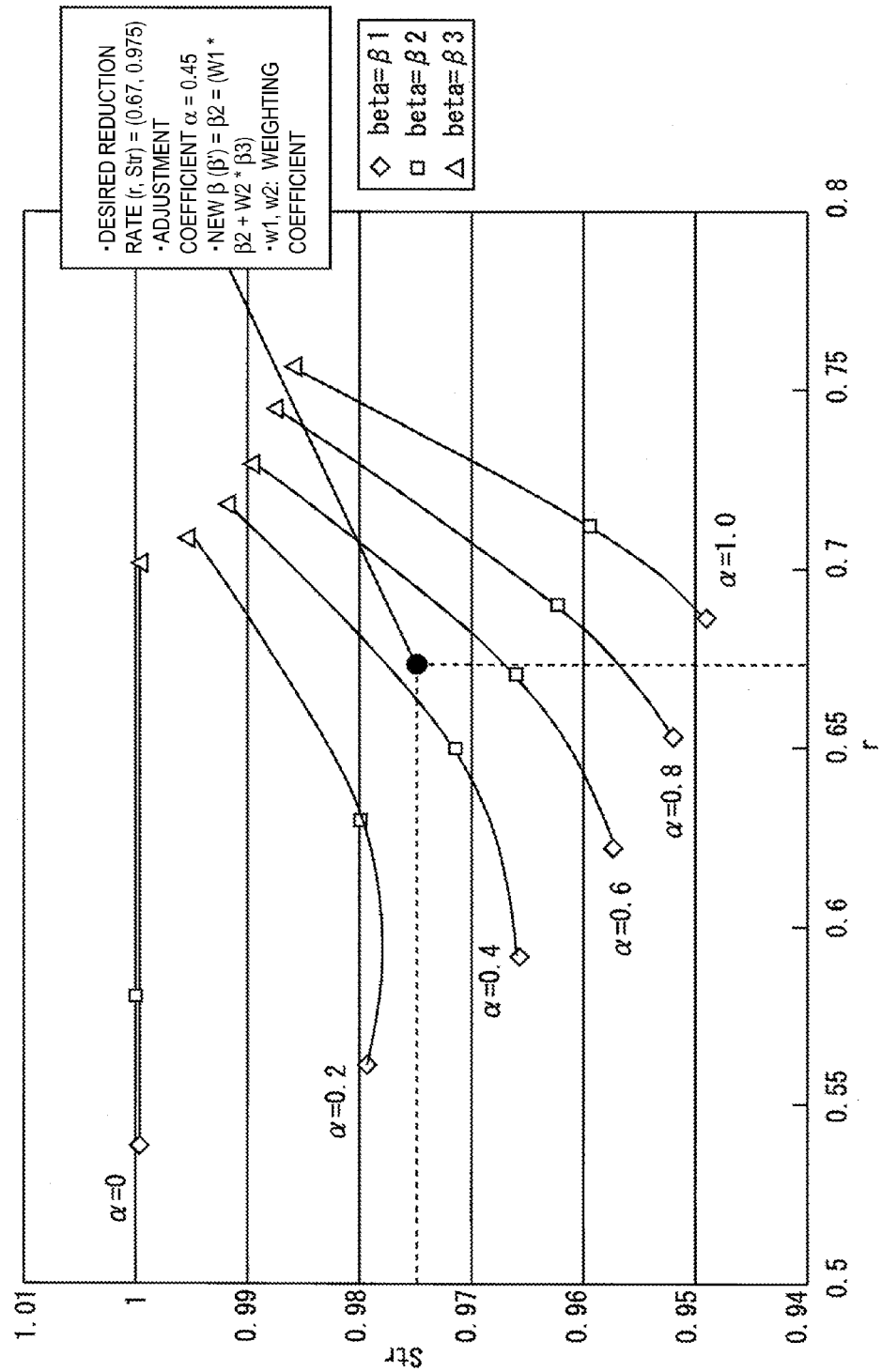
FIG. 12 is another example of relationship characteristic data.

When the strictly corresponding calibration coefficient (α, β) is not present in the relationship characteristic data 8, a calibration coefficient (α, β) having the closest value becomes a calculation result. Alternatively, an appropriate calibration coefficient (α, β) may be calculated by interpolation calculation using the peripheral data. FIG. 12 shows an example of calibration coefficient calculation when a strictly corresponding calibration coefficient combination is not present in the set image quality target values.

In the relationship characteristic data shown in FIG. 12, there is no combination of α and β corresponding to the desired image quality (r, Str)=(0.67, 0.975). Therefore, the reconstruction arithmetic device 221 calculates 0.45 as the adjustment coefficient α by interpolation calculation from the curve of α=0.4 and the curve of α=0.6, for example. Similarly for the correction coefficient β, a calculation is performed by applying a weighting coefficient to β2 and β3 to calculate the correction coefficient β.

Then, the reconstruction arithmetic device 221 acquires the projection data obtained in the previous step S308 (step S305). However, in the case of a first loop, initial projection data is acquired.

The acquired projection data is assumed to be Raw_C.

The reconstruction arithmetic device 221 calculates the noise-reduced projection data Raw_A by performing the noise reduction processing f1 on the acquired projection data Raw_C (step S306).

Raw_A is expressed by the following Equation (11).

$$\text{Raw\_A} = f1(\beta', \text{Raw\_C}) \tag{11}$$

In addition, the reconstruction arithmetic device 221 calculates the corrected projection data Raw_B by performing the signal strength maintenance processing f2 on the projection data Raw_C acquired in step S305 (step S307). Raw_B is expressed by the following Equation (12).

$$\text{Raw\_B} = f2(\beta', \text{Raw\_C}) \tag{12}$$

Then, the reconstruction arithmetic device 221 calculates the new projection data Raw_C from the Raw_A and the Raw_B using the adjustment coefficient α calculated in step S304 (step S308). Raw_C is expressed by the following Equation (13).

$$\text{Raw\_C} = f3(\alpha, \text{Raw\_A}, \text{Raw\_B}) \tag{13}$$

The reconstruction arithmetic device 221 repeats the processing in steps S305 to S309 until the set number of iterations ends. When the set number of iterations ends (step S309; Yes), the successive approximation projection data correction processing may be ended. In the determination regarding the end of the number of iterations, the reconstruction arithmetic device 221 may determine whether or not the iterative processing has ended by evaluating the amount of correction obtained by comparing the projection data before and after calibration processing.

As described above, in the successive approximation projection data correction processing of the present invention, the reconstruction arithmetic device 221 sets the number of iterations of the iterative processing for correcting the projection data, and calculates, as calibration coefficients, the correction coefficient β and the adjustment coefficient α for adjusting the application ratio of the noise reduction processing f1 and the signal strength maintenance processing f2 included in the iterative processing so that the image quality corresponding to the number of iterations is obtained. Then, corrected projection data is created by performing the above-described iterative processing (adjustment processing f3) on the projection data based on the number of iterations and the calibration coefficients, and the CT image is reconstructed. Accordingly, it is possible to appropriately adjust the noise reduction effect of the noise reduction processing f1 and the edge maintenance effect of the signal strength maintenance processing f2. As a result, it is possible to reconstruct an image in which the amount of noise is small and the generation of streak artifacts is suppressed.

In addition, since the relationship characteristic data showing the relationship between a parameter for adjusting noise and a parameter for adjusting the amount of streaks and the calibration coefficient (α, β) is stored and a calibration coefficient corresponding to the target image quality is calculated based on the relationship characteristic data, it is possible to correct the projection data so as to obtain a desired image quality by two kinds of image quality parameters having different characteristics.

First Embodiment

Next, a first embodiment will be described in detail with reference to FIGS. 13 to 24.

As described above, the relationship characteristic data showing the relationship between the calibration coefficient (α, β) and the image quality parameter may be created in the form of a look-up table.

FIG. 13 is an example of reference relationship characteristic data 8*a* in the form of a look-up table. The reference relationship characteristic data 8*a* is SD-St data in which the horizontal axis indicates the image SD value and the vertical axis indicates the streak amount St. Instead of this, a look-up table may be stored as r-Str data in which the horizontal axis indicates the noise reduction rate r and the vertical axis indicates the streak reduction rate Str.

The reference relationship characteristic data 8*a* is calculated in advance by the arithmetic device 202 in the same procedure as the relationship characteristic calculation processing shown in FIG. 7. The reconstruction arithmetic device 221 creates the reference relationship characteristic data 8*a* in the form of a look-up table by writing the relationship characteristic data 8 obtained by the processing in steps S101 to S109 in FIG. 7 in a table. For convenience of sampling, when the strictly corresponding α and β are not present, α and β having the closest values may be used or α and β may be recalculated by interpolation calculation as described above.

The reference relationship characteristic data 8*a* that is created in advance and is stored in the storage device 213 is created based on the projection data obtained by scanning using a phantom or the like, for example. The reconstruction arithmetic device 221 of the first embodiment creates updated relationship characteristic data 85 by finely adjusting the reference relationship characteristic data 8*a* so as to suit the features of the projection data. Then, the calibration coefficient (α, β) for obtaining the desired image quality (SD, St) is calculated using the updated relationship characteristic data 85.

Similar to the functional configuration shown in FIG. 5, the reconstruction arithmetic device 221 of the first embodiment includes a target image quality setting section 41, a number-of-iterations setting section 42, a relationship characteristic calculating section 43, a calibration coefficient calculating section 44, an iterative processing section 45, and an end determination section 46. The same components are denoted by the same reference numerals, and explanation thereof will be omitted.

Figure 14:
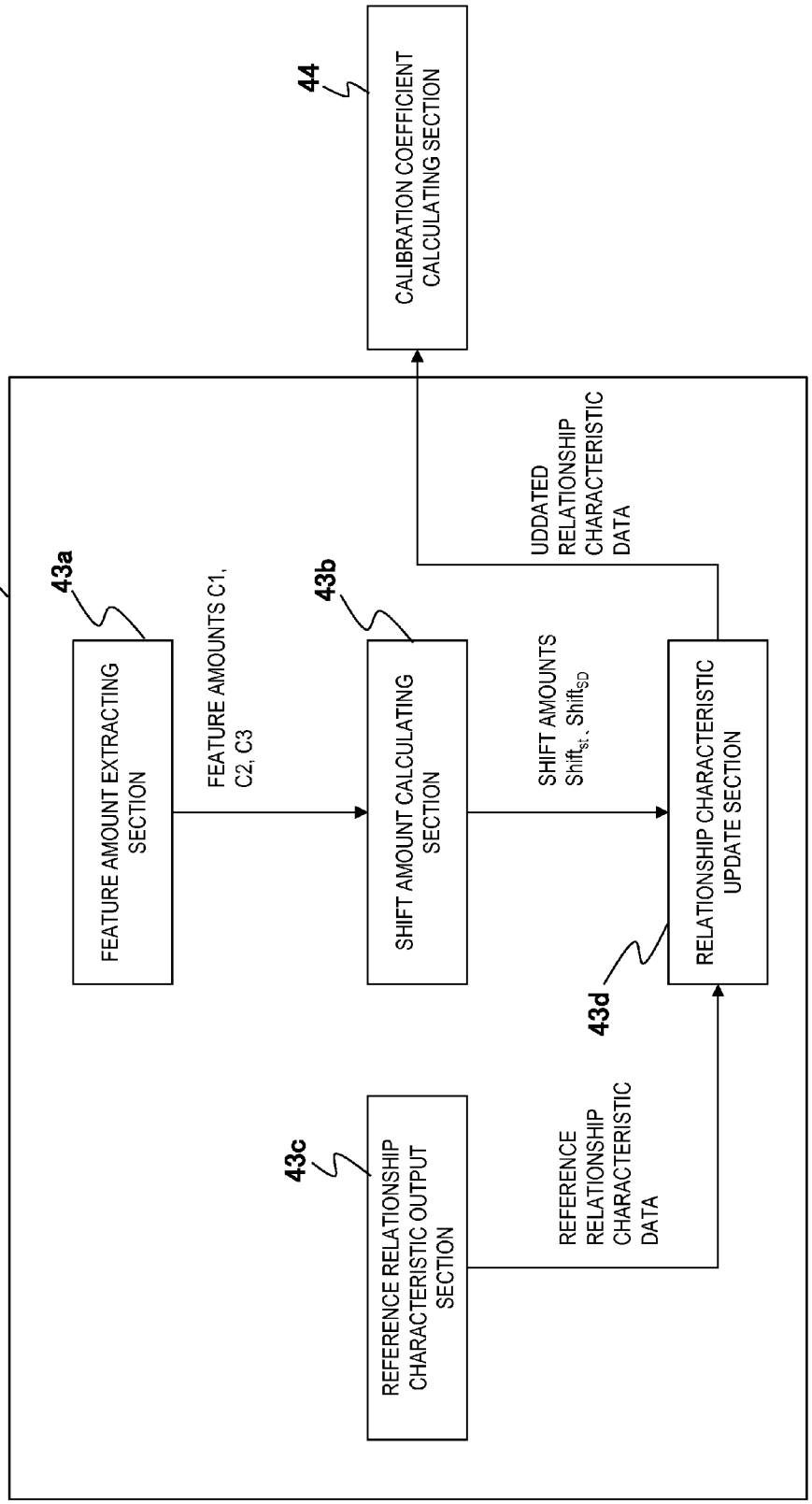
FIG. 14 is a block diagram showing the details of a relationship characteristic calculating section 43 of a first embodiment.

FIG. 14 is a functional block diagram for explaining the relationship characteristic calculating section 43 and the calibration coefficient calculating section 44 of the first embodiment.

The relationship characteristic calculating section 43 of the first embodiment includes a feature amount extracting section 43*a*, a shift amount calculating section 43*b*, a reference relationship characteristic output section 43*c*, and a relationship characteristic update section 43*d*.

The feature amount extracting section 43*a* extracts a feature amount of projection data to be corrected. Specifically, a first feature amount C1 regarding the size of a feature region 7 surrounded by a plurality of high absorber edges appearing in projection data, a second feature amount C2 regarding the shape of the feature region 7, and a third feature amount C3 regarding the magnitude of the projection value of the feature region 7 are extracted as feature amounts. The feature amount extracting section 43a calculates at least one or all of the feature amounts C1, C2, and C3 from the projection data.

Here, each of the feature amounts C1, C2, and C3 will be described with reference to FIGS. 15 to 18.

Figure 15:
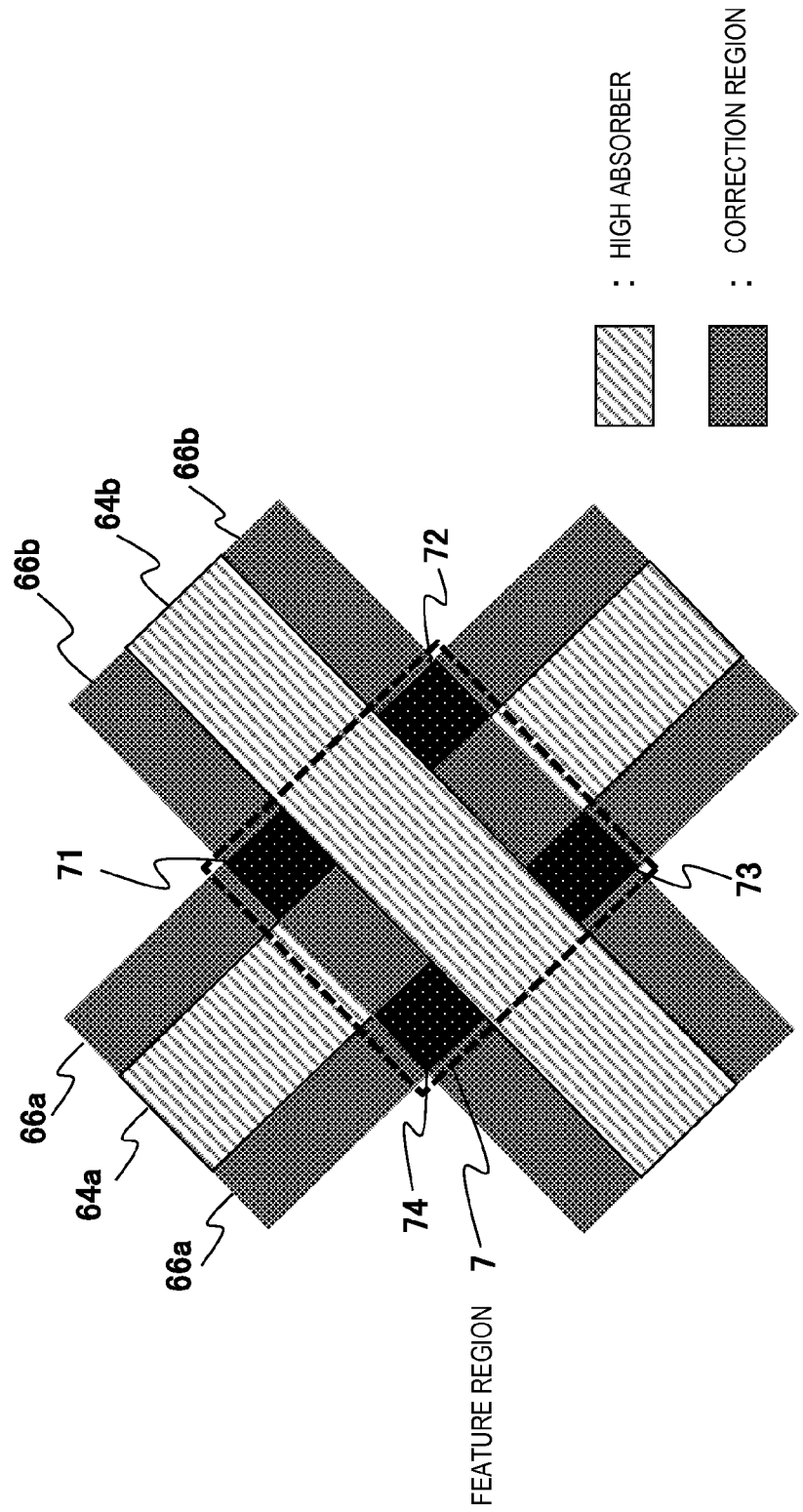
FIG. 15 is a diagram for explaining a feature region 7 of projection data.

FIG. 15 is a diagram for explaining the features appearing in projection data. When two high absorbers 64a and 64b are included in the scanning range, correction regions overlap each other in a portion where the two high absorbers 64a and 64b cross each other on the projection data. As a result, over-correction occurs. The portion where a plurality of high absorbers cross each other (inside of the broken line in FIG. 15) is assumed to be the feature region 7. A correction region generated by the noise reduction processing f1 overlaps corners 71, 72, 73, and 74 of the feature region 7. In particular, the corners 71, 72, 73, and 74 of the feature region 7 are easily over-corrected.

Therefore, the feature amount extracting section 43a sets a region, which is surrounded by the high absorber edges of projection data before correction, as the feature region 7, and extracts the size (for example, area) of the inside of the feature region 7 as the first feature amount C1. FIG. 16 is a diagram for explaining the first feature amount C1. As shown in FIG. 16(a), the area of the portion surrounded by the high absorber edges inside the feature region 7 is the feature amount C1. When the area (feature amount C1) is large as shown in FIG. 16(b), over-correction easily occurs when performing the noise reduction processing f1, compared with a case in which the area (feature amount C1) is small as shown in FIG. 16(c). This is because the data range that becomes smooth increases as the area increases.

The feature amount extracting section 43a extracts the shape of the feature region 7 as the second feature amount C2. For example, the ratio of the length of a channel direction axis (horizontal axis 75 in FIG. 17) and the length of a viewing direction axis (vertical axis 76 in FIG. 17) is extracted as shape features (second feature amount C2) of the feature region 7.

FIG. 17 is a diagram for explaining the second feature amount C2. As shown in FIG. 17(a), for example, a ratio of a length 75 of the feature region 7 in the channel direction and a length 76 of the feature region 7 in the viewing direction is assumed to be the second feature amount C2. Although it depends on the operation of the noise reduction processing, for example, in the case of performing an operation for weighted addition in the channel direction, over-correction occurs more easily in the case in which the length in the channel direction is larger than the length in the viewing direction as shown in FIG. 17(b) than in the case in which the length in the channel direction is smaller than the length in the viewing direction as shown in FIG. 17(c). This is because the amount of correction applied in the channel direction is large.

Figure 18:
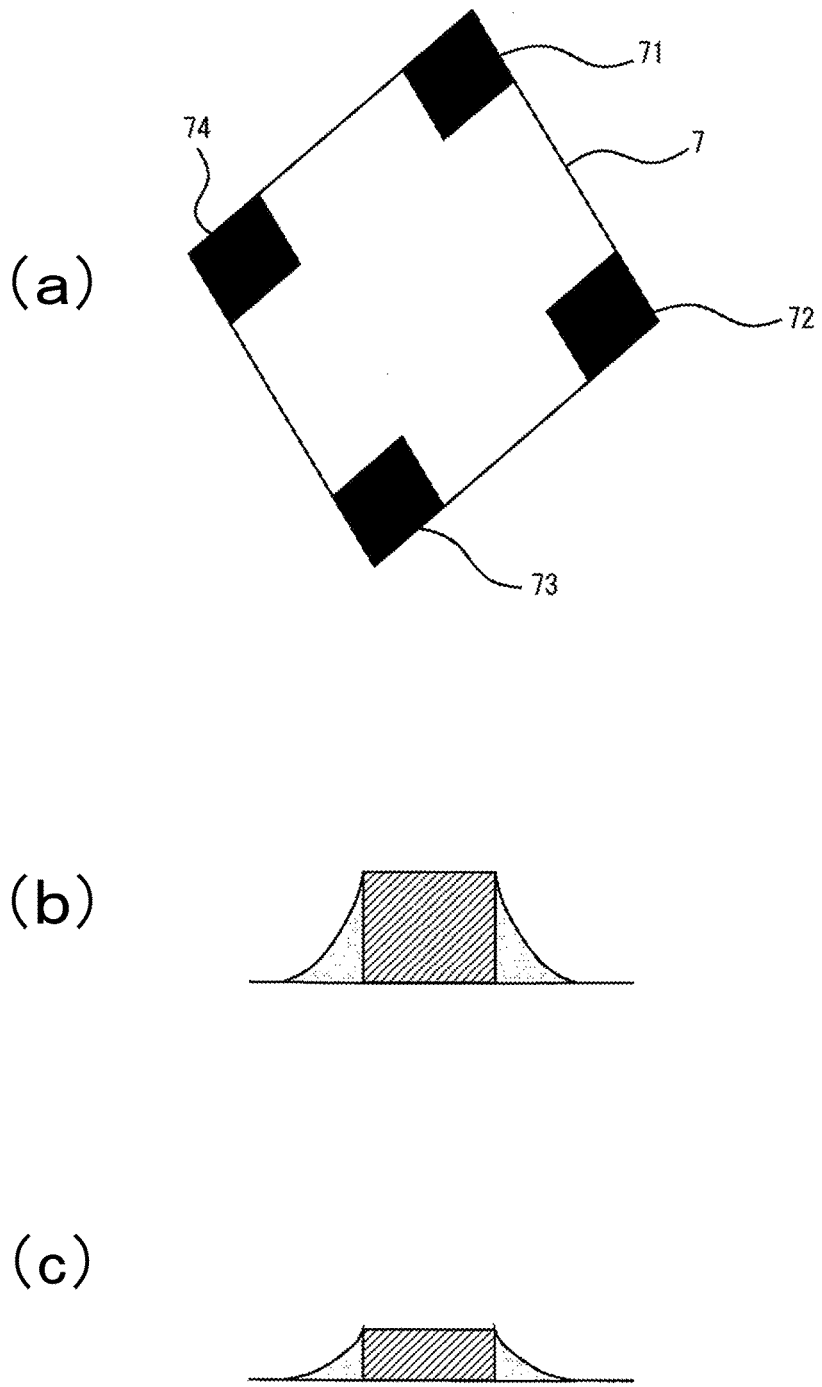
FIG. 18 is a diagram for explaining the feature amount C3.

In addition, the feature amount extracting section 43a extracts an average value of the projection values of the corners (area adjacent to a low absorption area in the feature region 7) of the feature region 7 as the third feature amount C3. FIG. 18 is a diagram for explaining the third feature amount C3. As shown in FIG. 18(a), an average value of the projection values of the corners 71, 72, 73, and 74 of the feature region 7 is the feature amount C3. When the average value (feature amount C3) of the projection values of the corners 71, 72, 73, and 74 is large as shown in FIG. 18(b), over-correction easily occurs when performing the noise reduction processing f1, compared with a case in which the feature amount C3 is small as shown in FIG. 18(c). This is because a gap between the high absorber and the periphery is large. The shape of the feature region 7 does not necessarily need to be a square. When the feature region 7 has a polygonal shape, an average value of the projection values of the corners near the apices is assumed to be the feature amount C3.

The shift amount calculating section 43b calculates the shift amount of each axis (SD, St) of a reference relationship characteristic table 8a corresponding to the feature amount.

A method of calculating the shift amount will be described with reference to FIGS. 19 to 22.

The shift amount calculating section 43b calculates the shift amounts $Shift_{St}$ and $Shift_{SD}$ of the image quality parameters St and SD for the feature amounts C1, C2, and C3 extracted by the feature amount extracting section 43a based on shift characteristic data 81 to 83.

The shift characteristic data 81 to 83 are calculated in advance for the feature amounts C1, C2, and C3, and are stored in the storage device 213.

Figure 19:
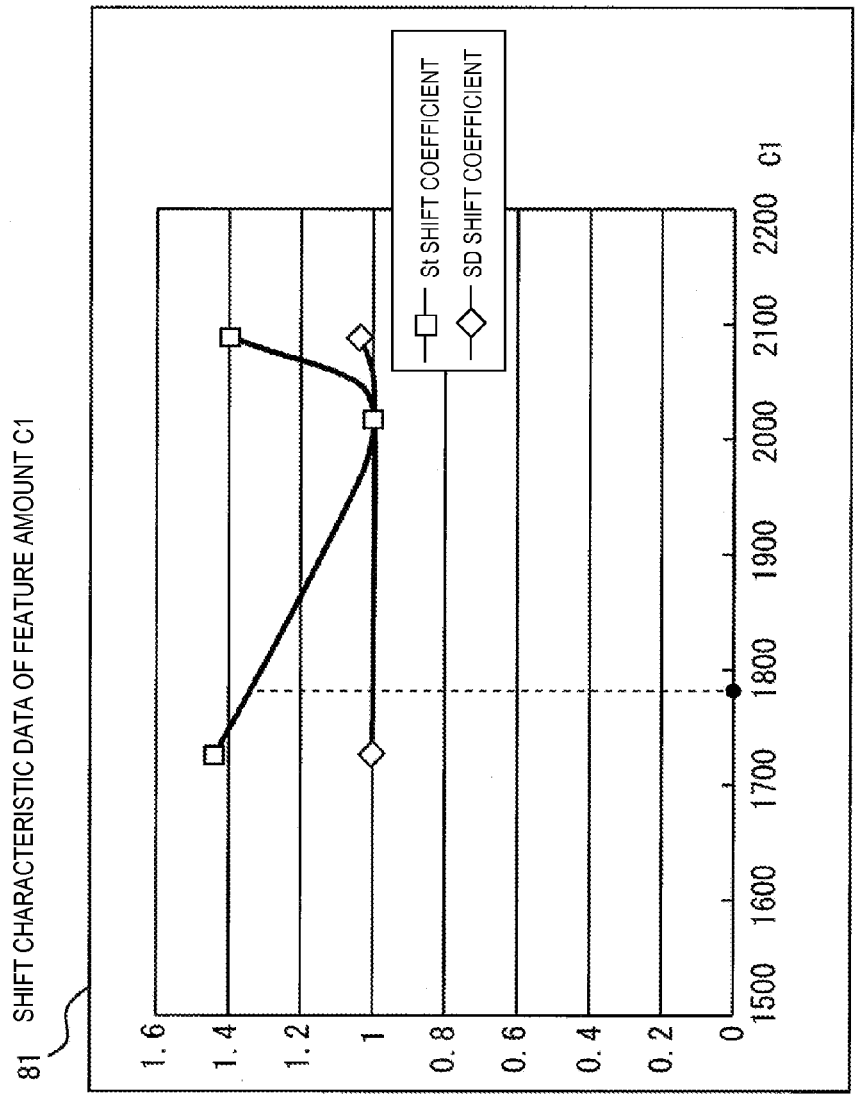
FIG. 19 is an example of shift characteristic data 81 of the feature amount C1.
Figure 20:
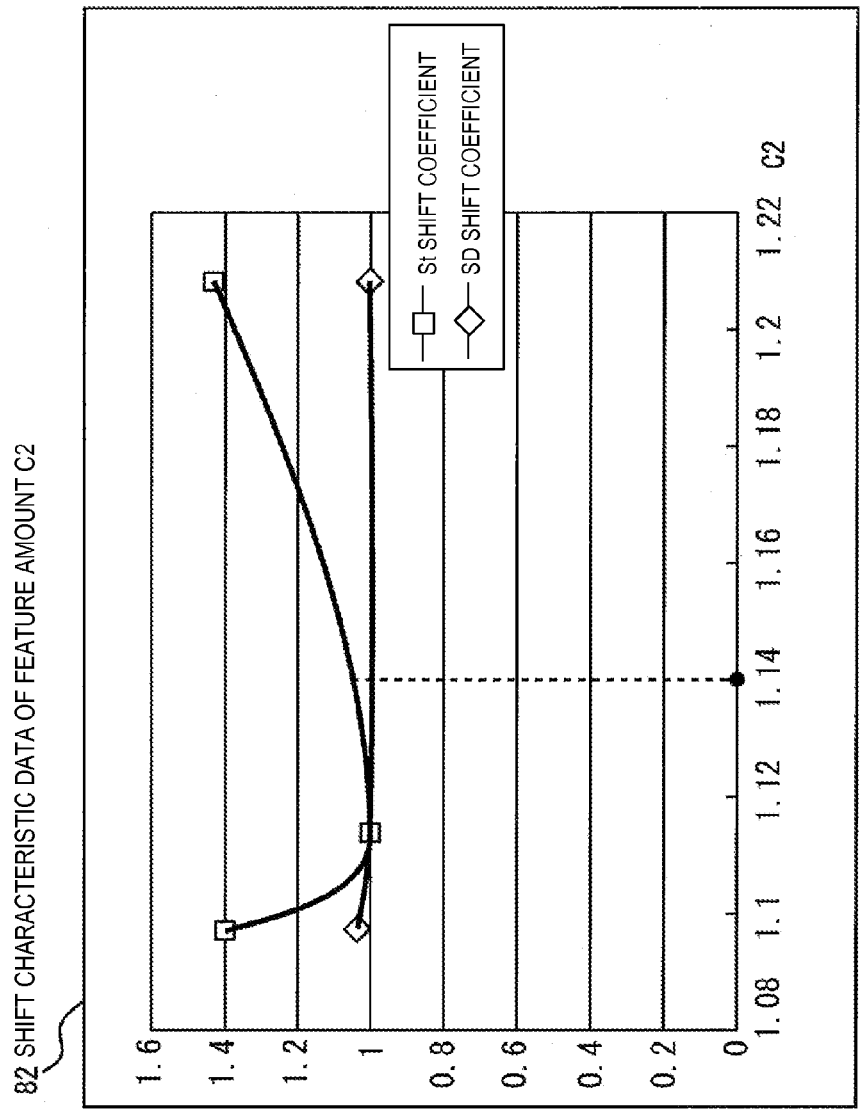
FIG. 20 is an example of shift characteristic data 82 of the feature amount C2.
Figure 21:
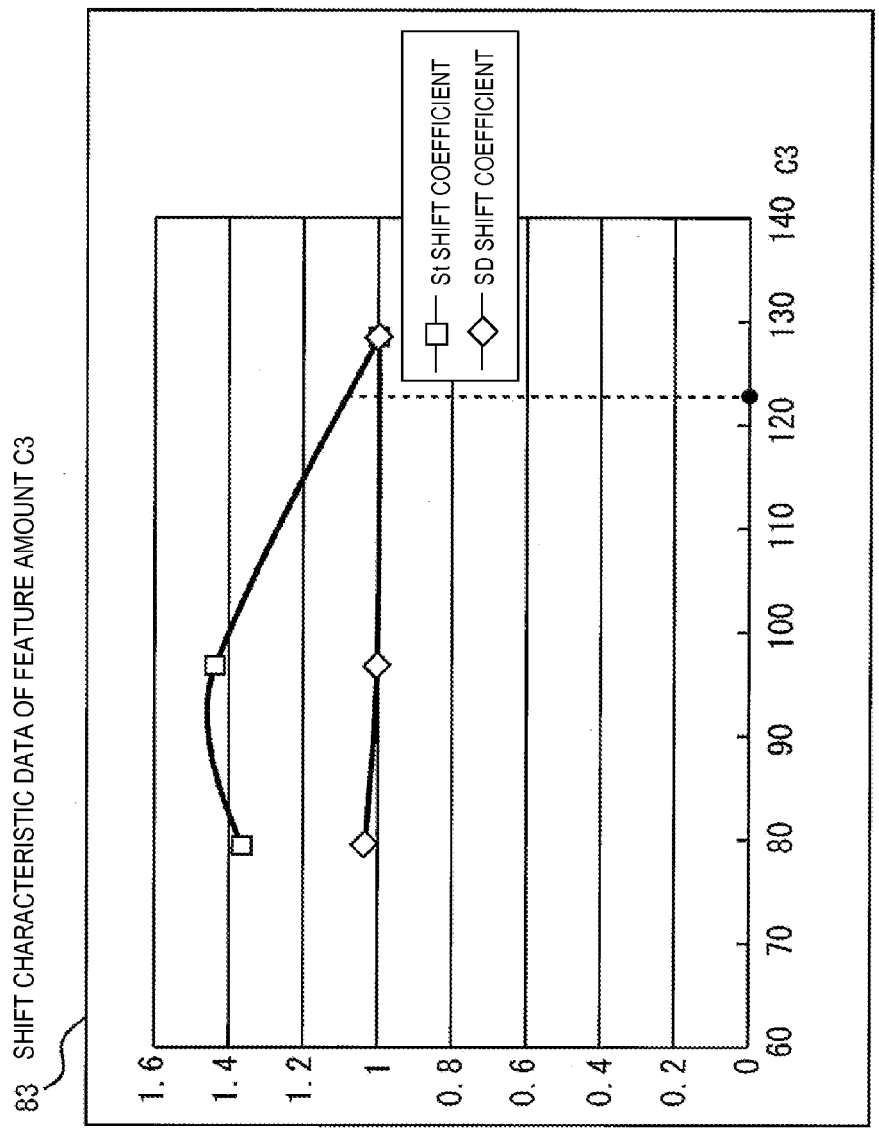
FIG. 21 is an example of shift characteristic data 83 of the feature amount C3.

FIG. 19 is an example of the shift characteristic data 81 of the first feature amount C1, FIG. 20 is an example of the shift characteristic data 82 of the second feature amount C2, and FIG. 21 is an example of the shift characteristic data 83 of the third feature amount C3. In each of the diagrams, the horizontal axis indicates the magnitude of the feature amount (C1, C2, C3), and the vertical axis indicates a ratio of the shift to the original data (shift coefficient).

For example, as shown in FIG. 19, when the value of the feature amount C1 is "1780", the St shift coefficient is approximately "1.3", and the SD shift coefficient is approximately "1". For example, as shown in FIG. 20, when the value of the feature amount C2 is "1.14", the St shift coefficient is approximately "1.04", and the SD shift coefficient is approximately "1". For example, as shown in FIG. 21, when the value of the feature amount C3 is "122", the St shift coefficient is approximately "1.1", and the SD shift coefficient is approximately "1".

In this manner, the shift amount calculating section 43b calculates the St shift coefficient and the SD shift coefficient for the feature amounts C1 to C3.

The shift amount calculating section 43b calculates the shift amounts $Shift_{SD}$ and $Shift_{St}$ of each axis (SD, St) by setting the weight (w1, w2, w3) as a shift coefficient for each of the feature amounts C1 to C3 and performing weighted addition.

The following Equation (14) is examples of calculating the weights w1, w2, and w3 of the St shift characteristics of the feature amounts C1, C2, and C3.

$$w1 = \frac{Shift_{st1}}{\sqrt{Shift_{st1}^2 + Shift_{st2}^2 + Shift_{st3}^2}}$$
$$w2 = \frac{Shift_{st2}}{\sqrt{Shift_{st1}^2 + Shift_{st2}^2 + Shift_{st3}^2}} \quad (14)$$
$$w3 = \frac{Shift_{st3}}{\sqrt{Shift_{st1}^2 + Shift_{st2}^2 + Shift_{st3}^2}}$$

The St shift amount $Shift_{St}$ is calculated by the following Equation (15).

$$Shift_{St} = w1 \cdot Shift_{st1} + w2 \cdot Shift_{st2} + w3 \cdot Shift_{st3} \quad (15)$$

Similarly, the SD shift amount $Shift_{SD}$ is calculated by the following Equation (16).

$$Shift_{SD} = w1 \cdot Shift_{SD1} + w2 \cdot Shift_{SD2} + w3 \cdot Shift_{SD3} \quad (16)$$

Figure 22:
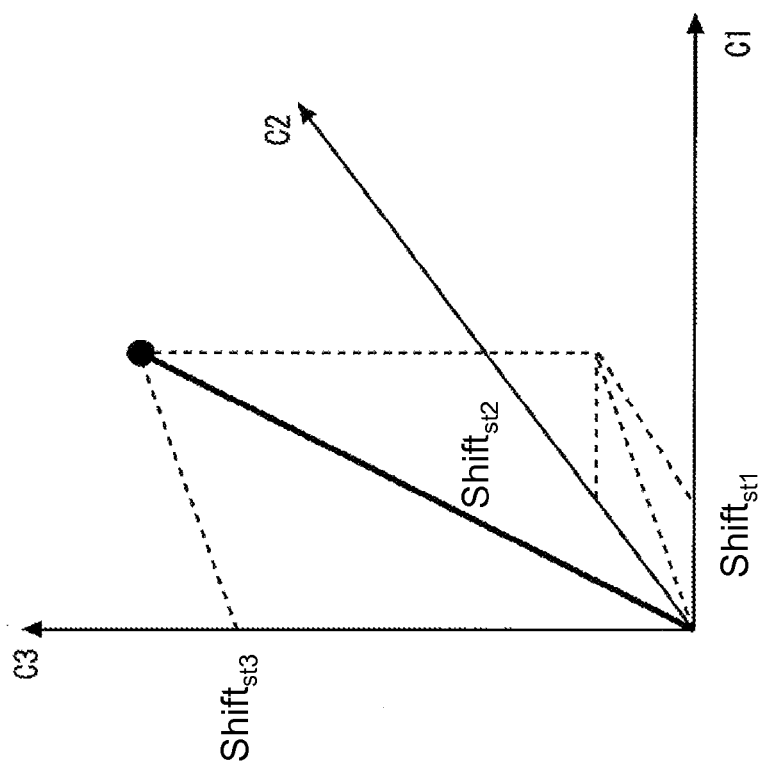
FIG. 22 is a calculation example of a shift amount $Shift_{St}$ that is calculated according to the feature amounts C1 to C3.

The shift amount $Shift_{St}$ when the three feature amounts C1 to C3 are taken into consideration is expressed in a three-dimensional coordinate space, as shown in FIG. 22. The same is true for the $Shift_{SD}$.

The shift amount calculating section 43b outputs the calculated shift amount to the relationship characteristic update section 43d. In addition, the reference relationship characteristic output section 43c acquires the reference relationship characteristic table 8a stored in the storage device 213, and outputs the reference relationship characteristic table 8a to the relationship characteristic update section 43d.

The relationship characteristic update section 43d calculates an updated relationship characteristic table 85 suitable for the target projection data by updating (shifting) the reference relationship characteristic table 8a based on the shift amounts $Shift_{SD}$ and $Shift_{St}$ calculated by the shift amount calculating section 43b.

Figure 23:
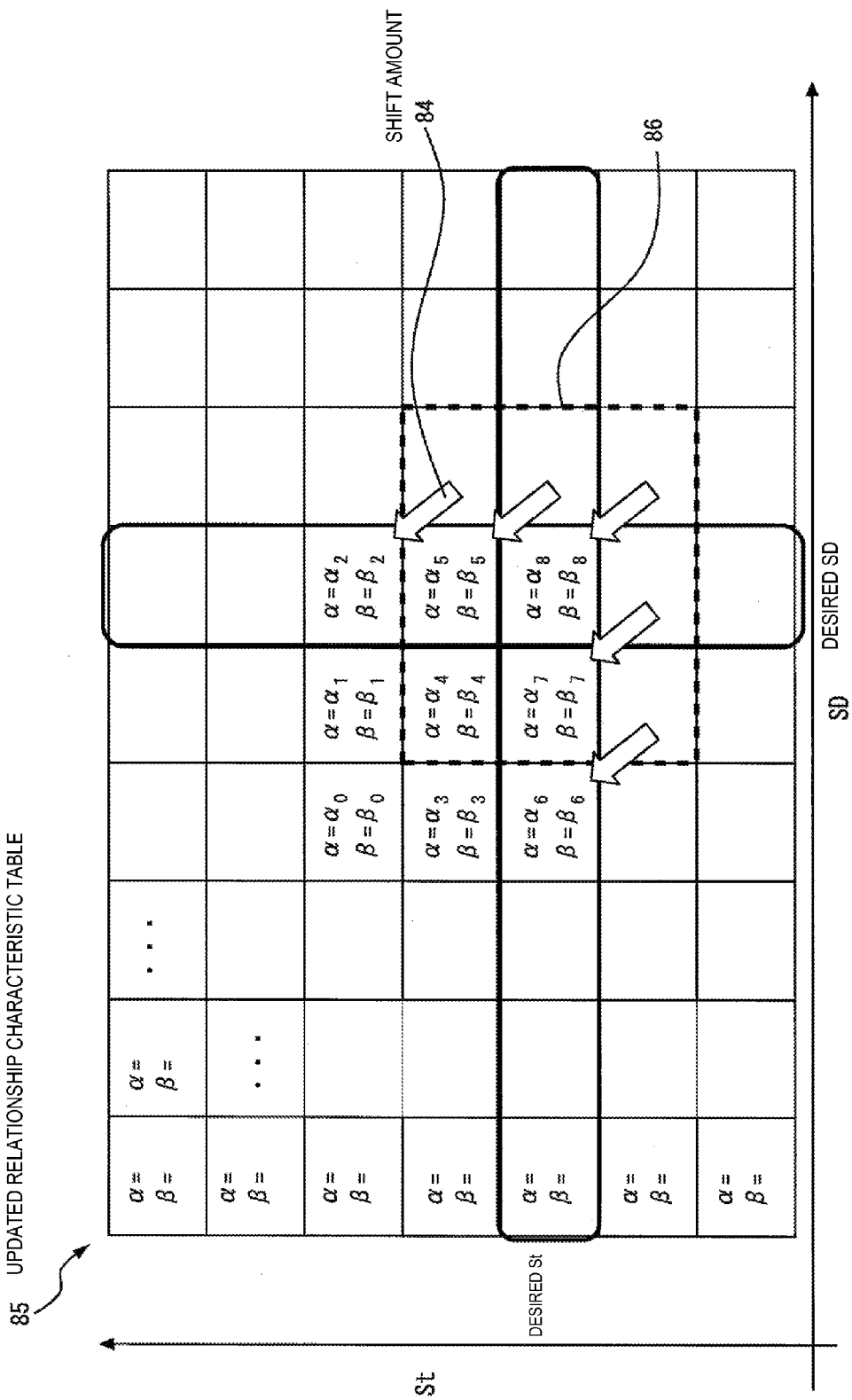
FIG. 23 is an example of an updated relationship characteristic table 85.

FIG. 23 is an example of the updated relationship characteristic table 85. In FIG. 23, the arrow 84 indicates a shift amount. In the reference relationship characteristic table 8a shown in FIG. 13, data present at a position shown by a dotted frame 86 is shifted by the shift amounts $Shift_{SD}$ and $Shift_{St}$ corresponding to the feature amounts (moved by the distance shown by the arrow 84). As a result, the calibration coefficients ($\alpha$, $\beta$) corresponding to the desired SD value and the desired streak amount St are correctly calculated for each piece of projection data.

The flow of the calibration coefficient calculation processing of the first embodiment will be described with reference to the flowchart shown in FIG. 24. The calibration coefficient calculation processing shown in FIG. 24 is a process corresponding to the processing in step S304 of the successive approximation projection data correction processing shown in FIG. 11.

The reference relationship characteristic table 8a is assumed to be stored in the storage device 213. In addition, it is assumed that, through the processing in steps S301 to S303 in FIG. 11, projection data is acquired, the target image qualities SD and St are set, and the number of iterations of the iterative processing is set.

Figure 24:
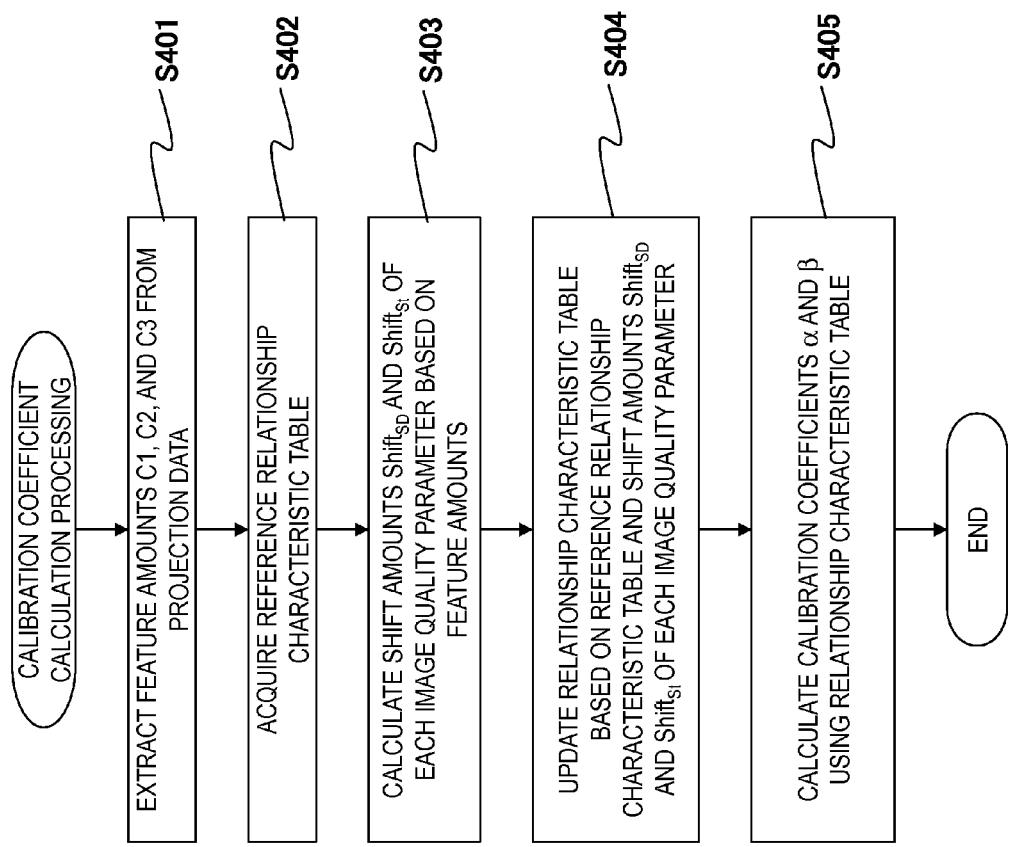
FIG. 24 is a flowchart showing the procedure of calibration coefficient calculation processing of the first embodiment.

In the calibration coefficient calculation processing shown in FIG. 24, first, the reconstruction arithmetic device 221 extracts the feature amounts C1, C2, and C3 from the projection data (step S401). As described above, the feature amount C1 is the area of an intersection portion (feature region 7) of the high absorber edges included in the projection data, the feature amount C2 is an aspect ratio of the feature region 7, and the feature amount C3 is an average projection value of the corners of the feature region 7. When a plurality of feature regions 7 are present in the projection data, the feature amounts C1, C2, and C3 are calculated for each of the feature regions 7.

The reconstruction arithmetic device 221 acquires the reference relationship characteristic table 8a from the storage device 213 (step S402). For example, the reference relationship characteristic table 8a in the form of a look-up table as shown in FIG. 13 is acquired.

The reconstruction arithmetic device 221 calculates the shift amounts $Shift_{SD}$ and $Shift_{St}$ of each axis (SD axis, St axis) based on the feature amounts C1, C2, and C3 calculated in step S401 (step S403). The shift amounts $Shift_{SD}$ and $Shift_{St}$ can be calculated based on the shift characteristics (FIGS. 19 to 21) calculated in advance for each of the feature amounts C1, C2, and C3. That is, the shift amount $Shift_{SD}$ is calculated by performing weighted addition of shift coefficients $Shift_{SD1}$ to $Shift_{SD3}$ calculated from the shift characteristic data. Similarly, the shift amount $Shift_{St}$ is calculated by performing weighted addition of shift coefficients $Shift_{St1}$ to $Shift_{St3}$ calculated from the shift characteristic data. Equations for calculating the shift amounts $Shift_{St}$ and $Shift_{SD}$ are Equations (14) to (16) described above.

The reconstruction arithmetic device 221 creates the updated relationship characteristic table 85 by updating the reference relationship characteristic table 8a based on the shift amounts $Shift_{SD}$ and $Shift_{St}$ for the image quality parameters SD and St (step S404). Therefore, it is possible to obtain the updated relationship characteristic table corresponding to the features of the projection data.

The reconstruction arithmetic device 221 calculates a calibration coefficient ($\alpha$, $\beta$) corresponding to the desired SD value and the desired streak amount St using the updated relationship characteristic table 85 (step S405).

Figure 11:
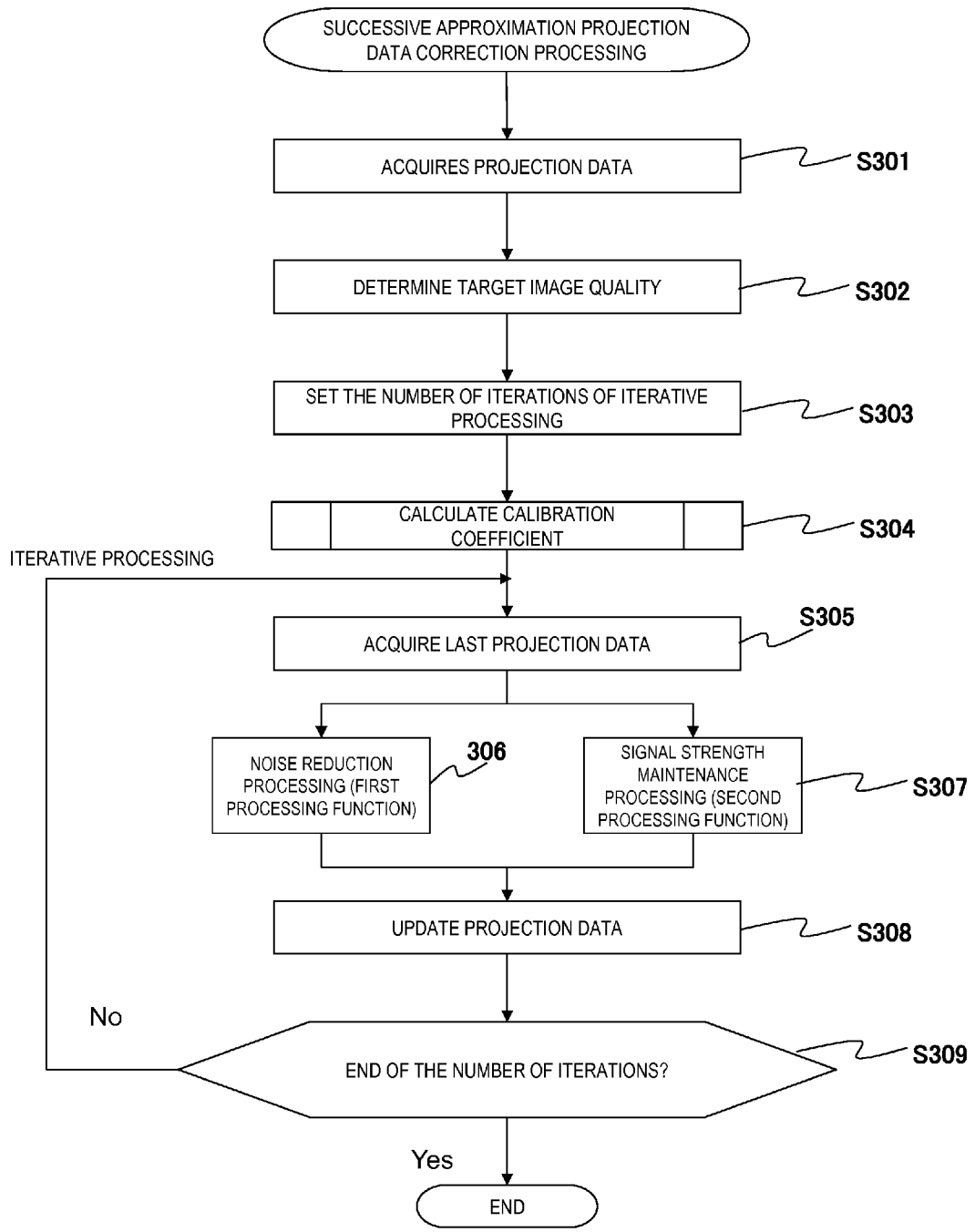
FIG. 11 is a flowchart showing the procedure of successive approximation projection data correction processing.

After the calibration coefficient ($\alpha$, $\beta$) is calculated, the reconstruction arithmetic device 221 calculates corrected projection data by executing the iterative processing in steps S305 to S309 in FIG. 11.

As described above, according to the first embodiment, the reference relationship characteristic table 8a as a reference that shows the relationship between the parameter SD regarding the amount of noise and the parameter St regarding the amount of streaks and the calibration coefficient ($\alpha$, $\beta$) is stored in the storage device 213, and the calibration coefficient ($\alpha$, $\beta$) is calculated after finely adjusting the reference relationship characteristic table 8a according to the feature amounts C1, C2, and C3 of the projection data of the actual object. Therefore, it is possible to calculate a calibration coefficient suitable for the features of projection data. As a result, it is possible to perform correction corresponding to the features of projection data.

Second Embodiment

Figure 25:
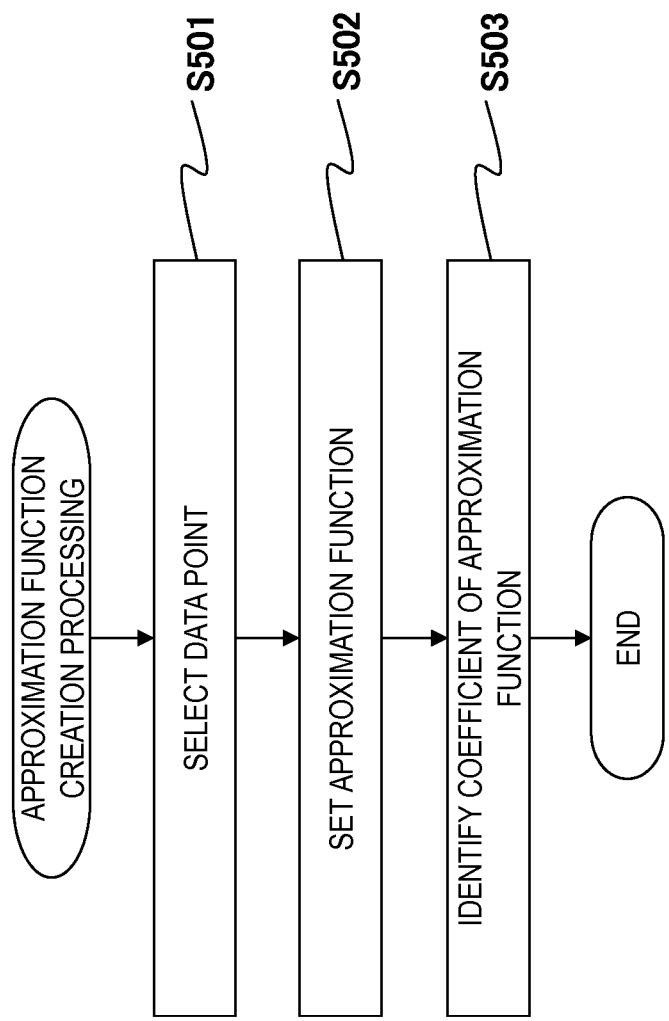
FIG. 25 is a flowchart for explaining the procedure of approximation function creation processing of a second embodiment.

Next, a second embodiment will be described in detail with reference to FIG. 25.

In the second embodiment, an example for storing the relationship characteristic data 8 in an approximation function will be described.

Figure 2:
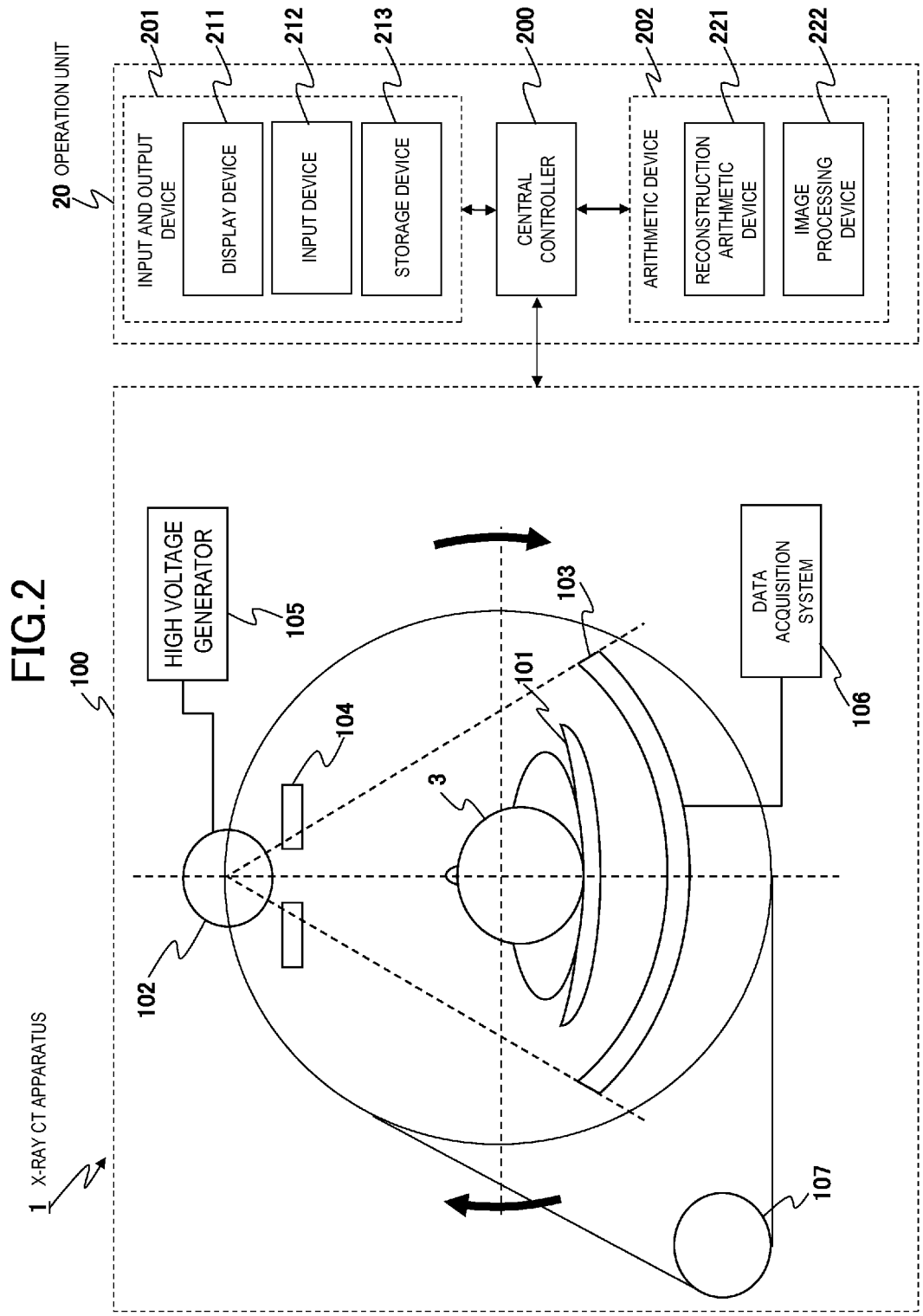
FIG. 2 is a hardware block diagram of the X-ray CT apparatus 1.

The hardware configuration and functional configuration of the arithmetic device 202 of the second embodiment are the same as those in FIGS. 1, 2, and 5. In the following explanation, the same components are denoted by the same reference numerals, and repeated explanation thereof will be omitted.

The relationship characteristic data 8 is calculated by the reconstruction arithmetic device 221 in the procedure of the relationship characteristic calculation processing shown in FIG. 7. The reconstruction arithmetic device 221 performs approximation function creation processing shown in FIG. 25, when the relationship characteristic data 8 is created by the processing in steps S101 to S108 in FIG. 7.

The reconstruction arithmetic device 221 selects an arbitrary number of data points from the relationship characteristic data 8 (step S501). The selected data point is described as ($\alpha_i$, $\beta_i$, $r_i$, $Str_i$). i is a positive integer (1, ..., n).

Then, the reconstruction arithmetic device 221 sets an approximation function that approximates the relational equation of the adjustment coefficient $\alpha$, the correction coefficient $\beta$, the noise reduction rate r, and the streak reduction rate Str (step S502). For example, the approximation function is the following Equation (17). k, l, and m are coefficients for calculating a from r and Str.

$$\alpha = k \cdot r + l \cdot Str + m \quad (17)$$

Then, the reconstruction arithmetic device 221 identifies the coefficients k, l, and m of the approximation function (step S503).

Assuming that a difference between the data points ($\alpha_i$, $r_i$, $Str_i$) and the approximation function is $d_i$, $d_i$ is expressed by the following Equation (18).

$$d_i = k \cdot r_i + l \cdot Str_i + m - \alpha_i \qquad (18)$$

The sum S of the squares of the difference $d_i$ between all data points and the approximation function is expressed by the following Equation (19).

$$S = \sum_{i=1}^{n} d_i = \sum_{i=1}^{n} (k \cdot r_i + l \cdot Str_i + m - \alpha_i)^2 \qquad (19)$$

The reconstruction arithmetic device 221 calculates k, l, and m that minimize S satisfying the following Equation (20). When a solution cannot be found strictly, a value converged by the iterative calculation is set as a solution.

$$\frac{\partial S}{\partial k} = 0, \ \frac{\partial S}{\partial l} = 0, \ \frac{\partial S}{\partial m} = 0 \qquad (20)$$

The reconstruction arithmetic device 221 determines the approximation function by substituting the calculated k, l, and m into Equation (17) described above.

It is possible to calculate β from r and Str in the same method.

When the approximation function is created by the processing in steps S501 to S503, the reconstruction arithmetic device 221 stores the approximation function in the storage device 213.

The created approximation function is used for the calculation of the calibration coefficient (α, β) by being referred to in the calibration coefficient calculation processing (step S304) of the successive approximation projection data correction processing shown in FIG. 11.

In the above explanation, the order of the approximation function is a first order. However, the order of the approximation function is not limited thereto. As the order increases, the accuracy improves. Although the example of calculating the approximation function showing the relationship between the noise reduction rate r and the streak reduction rate Str and the adjustment coefficient α or the correction coefficient β is shown, an approximation function showing the relationship between the image SD value and the streak amount St and the adjustment coefficient α or the correction coefficient β may be calculated.

By storing the relationship characteristic data in the form of an approximation function as in the second embodiment, it is possible to suppress the memory capacity, compared with the case of storing the relationship characteristic data in the form of a look-up table as in the first embodiment.

Third Embodiment

Figure 26:
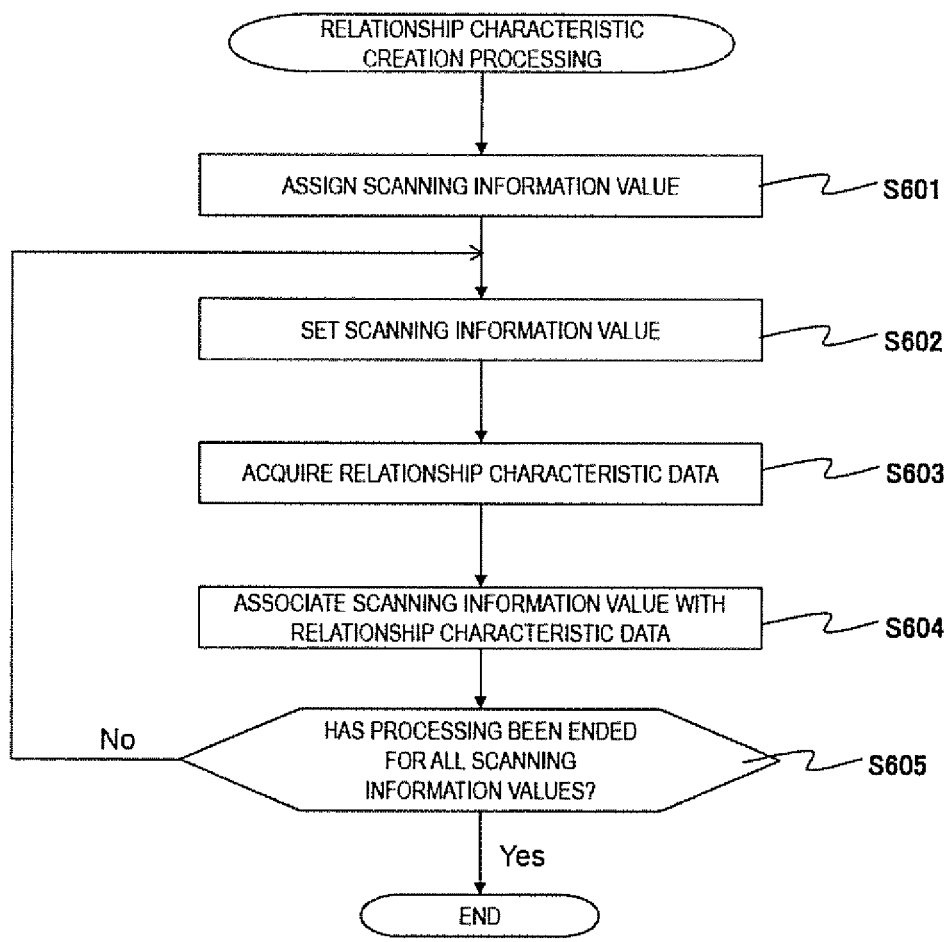
FIG. 26 is a flowchart for explaining the procedure of relationship characteristic creation processing of a third embodiment.

Next, a third embodiment will be described in detail with reference to FIGS. 26 to 28.

In the third embodiment, an example of creating relationship characteristic data for each of the scanning conditions and storing the relationship characteristic data in the storage device 213 will be described.

The tendency of streak artifacts differs depending on the scanning conditions. For example, the amount of streak artifacts is large in the shoulder or the lower limb, but is small in the abdomen. When the tube voltage at the time of scanning is low, there is a tendency that the amount of streak artifacts increases, compared with a case in which the tube voltage is high. Therefore, in the case of calculating the calibration coefficient (α, β) for projection data, which is obtained by scanning different parts or obtained by performing scanning under the different scanning conditions, using the same relationship characteristic data at all times and correcting the projection data by applying the calibration coefficient (α, β), variations occur in the streak reduction effect or the noise reduction effect of the image.

Therefore, in the third embodiment, the relationship characteristic data is created for each of the scanning conditions. In addition, in the successive approximation projection data correction processing, the calibration coefficient is calculated with reference to the appropriate relationship characteristic data according to the scanning conditions of the target projection data.

First, relationship characteristic creation processing of the third embodiment will be described with reference to FIG. 26.

First, the reconstruction arithmetic device 221 assigns the value of all of the scanning conditions as a scanning information value sp (step S601). The scanning conditions refer to the combination of various kinds of conditions including X-ray conditions such as a tube voltage and a tube current, conditions regarding scanning such as a pitch and collimator conditions, scanning parts such as a head, neck, shoulder, chest, abdomen, and lower limb, and reconstruction conditions such as a reconstruction slice thickness. The scanning information value sp is identification information assigned for each of the scanning conditions or data generated from the values of the scanning conditions themselves.

Then, the reconstruction arithmetic device 221 associates the scanning information value sp and the relationship characteristic data with each other.

That is, the reconstruction arithmetic device 221 sets one arbitrary scanning information value sp (step S602). The reconstruction arithmetic device 221 acquires projection data scanned under the scanning conditions corresponding to the scanning information value sp and executes the relationship characteristic calculation processing shown in FIG. 7 to create relationship characteristic data (step S603). The reconstruction arithmetic device 221 associates the scanning information value sp and the relationship characteristic data acquired in step S603, and stores the result in the storage device 213 (step S604).

The reconstruction arithmetic device 221 determines whether or not the acquisition and association of relationship characteristic data for all of the scanning information values sp have been ended (step S605). When there is the scanning information value sp that has not yet been processed (step S605; No), the process returns to step S602. The reconstruction arithmetic device 221 sets the next scanning information value sp, calculates relationship characteristic data from the projection data corresponding to the scanning information value sp, and associates the scanning information value sp and the relationship characteristic data with each other. When the processing for all of the scanning information values sp is ended by repeating the processing in steps S602 to S604 while changing the scanning information value sp (step S605; Yes), the relationship characteristic creation processing shown in FIG. 26 is ended.

Figure 27:
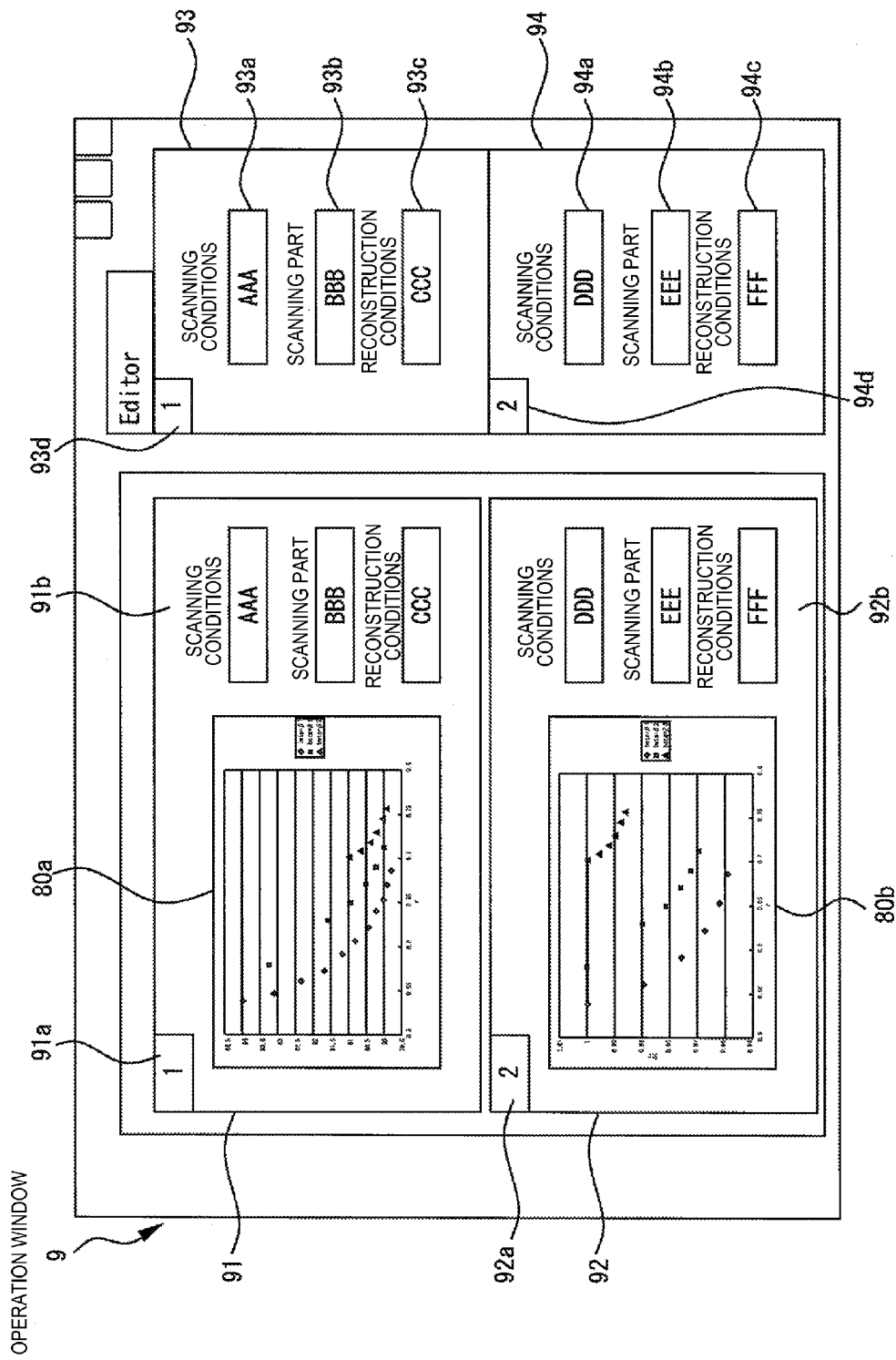
FIG. 27 is an example of an operation window 9 for associating the scanning conditions with relationship characteristic data.

The reconstruction arithmetic device 221 may display an operation window 9 shown in FIG. 27 on the display device 211.

The operation window 9 shown in FIG. 27 has relationship characteristic data display areas 91 and 92 and editing areas 93 and 94. Scanning information values sp 91a and 91b and relationship characteristic data 80a associated with the scanning information values sp 91a and 91b are displayed in the relationship characteristic data display area 91. Similarly, other scanning information values sp 92a and 92b and relationship characteristic data 80b associated with the scanning information values sp 92a and 92b are displayed in the lower relationship characteristic data display area 92. A scanning condition input column 93a, a scanning part input column 93b, a reconstruction condition input column 93c, a scanning information value input column 93d, and the like are provided in the editing area 93. Similarly, a scanning condition input column 94a, a scanning part input column 94b, a reconstruction condition input column 94c, a scanning information value input column 94d, and the like are provided in the lower editing area 94.

In the relationship characteristic data display area 91 of the operation window 9, for example, the scanning conditions 91b assigned for the scanning information value sp="1" are displayed. In addition, the relationship characteristic data 80a created based on the projection data obtained by scanning under the scanning conditions 91b is displayed. In the editing area 93, the same information (scanning information value sp) as the information displayed in the relationship characteristic data display area 91 is displayed in the input columns 93a to 93d. When the values of the input columns 93a to 93d are changed by the operator, the changed content is reflected on the information displayed in the relationship characteristic data display area 91. In addition, the scanning information value sp, the scanning conditions, and the relationship characteristic data are associated with each other with the changed content, and are stored.

Various scanning conditions and the relationship characteristic data are associated with each other by the above procedure.

Next, the flow of the entire process of the X-ray CT apparatus 1 of the third embodiment will be described with reference to FIG. 28.

First, the X-ray CT apparatus 1 performs positioning scanning for the object 3. Then, the X-ray CT apparatus sets various conditions, such as scanning conditions or reconstruction conditions, based on a positioning image captured by the positioning scanning. Then, the X-ray CT apparatus 1 performs tomography (main scanning), thereby acquiring projection data (step S701).

It is preferable that the reconstruction arithmetic device 221 records scanning conditions (scanning information value sp) in the acquired projection data for each scanning range (for example, for each view) (step S702).

The reconstruction arithmetic device 221 performs successive approximation projection data correction processing on the acquired projection data (step S703). The procedure of the successive approximation projection data correction processing in step S703 is the same as the procedure shown in FIG. 11. For the calibration coefficient calculation processing in step S304 in FIG. 11, the reconstruction arithmetic device 221 of the third embodiment performs the calibration coefficient calculation processing shown in FIG. 29.

Figure 29:
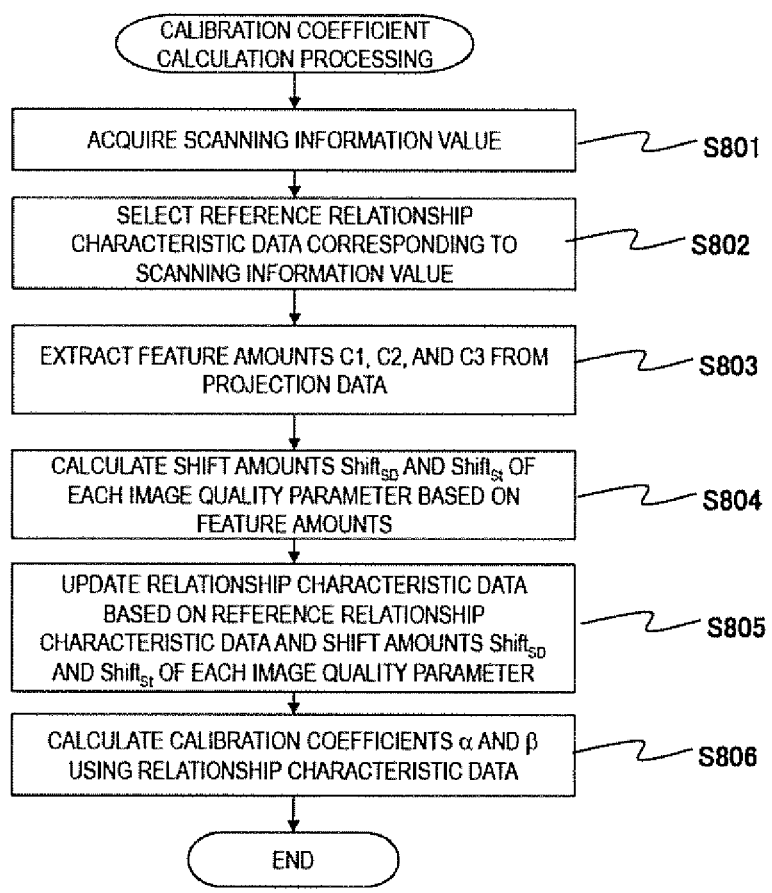
FIG. 29 is a flowchart showing the procedure of calibration coefficient calculation processing of the third embodiment.

The calibration coefficient calculation processing of the third embodiment will be described with reference to FIG. 29.

The reconstruction arithmetic device 221 acquires the scanning information value sp (scanning conditions) recorded in the projection data (step S801). The reconstruction arithmetic device 221 selects reference relationship characteristic data corresponding to the acquired scanning information value sp from the storage device 213 (step S802). When different scanning conditions (scanning information value sp) are recorded for each scanning range (for example, for each view) of projection data, the reconstruction arithmetic device 221 selects reference relationship characteristic data corresponding to all of the recorded scanning information values sp from the storage device 213.

The reconstruction arithmetic device 221 calculates the calibration coefficient ($\alpha$, $\beta$) based on the reference relationship characteristic data and the set target image quality (SD, st).

As in the first embodiment, the reconstruction arithmetic device 221 may update the reference relationship characteristic data acquired in step S802 according to the features of the projection data. In this case, first, the reconstruction arithmetic device 221 extracts the feature amounts C1, C2, and C3 from the projection data (step S803), and calculates the shift amounts $Shift_{SD}$ and $Shift_{St}$ based on the feature amounts C1, C2, and C3 (step S804). The method of calculating the shift amounts $Shift_{SD}$ and $Shift_{St}$ is the same as that of the first embodiment.

The reconstruction arithmetic device 221 updates the reference relationship characteristic data acquired in step S802 based on the shift amounts $Shift_{SD}$ and $Shift_{St}$ of each image quality parameter (step S805). The reconstruction arithmetic device 221 calculates the calibration coefficient ($\alpha$, $\beta$) corresponding to the desired SD value and the desired streak amount St using the updated relationship characteristic data (step S806).

After the calibration coefficient ($\alpha$, $\beta$) is calculated as described above, the reconstruction arithmetic device 221 calculates corrected projection data by executing the iterative processing in steps S305 to S309 in FIG. 11.

Figure 28:
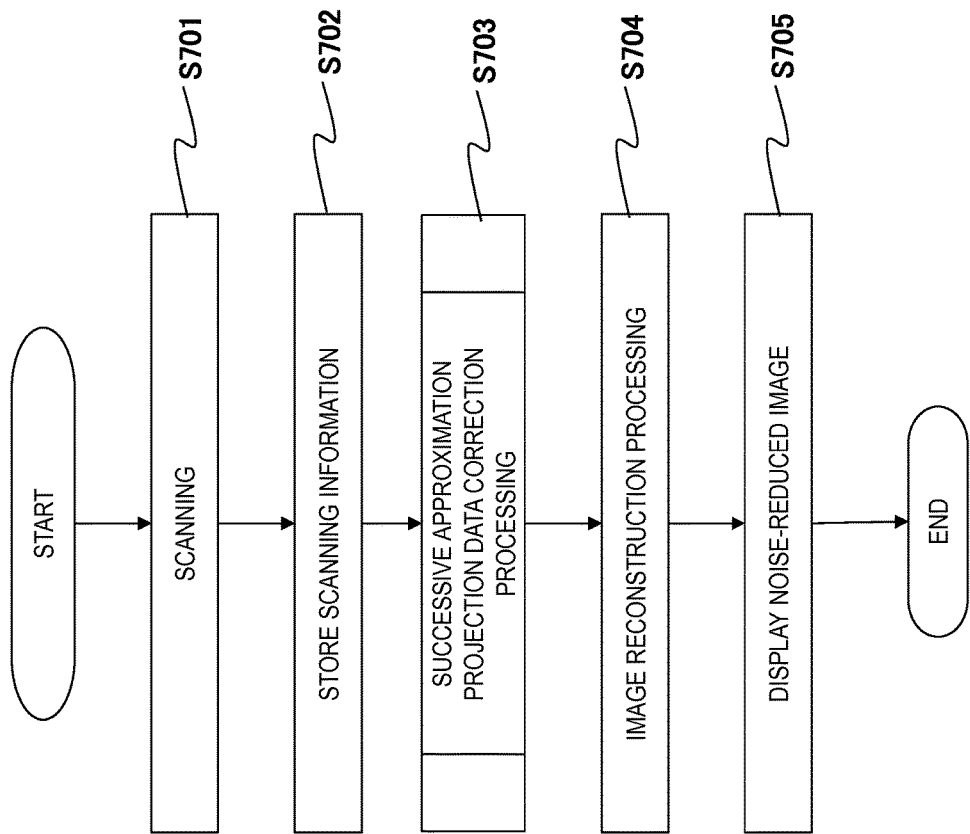
FIG. 28 is a flowchart for explaining the flow of the overall processing of the third embodiment.

The reconstruction arithmetic device 221 generates a CT image by performing image reconstruction using the corrected projection data that has been corrected by the successive approximation projection data correction processing (step S704 in FIG. 28). The reconstruction arithmetic device 221 displays the generated CT image on the display device 211 (step S705).

As described above, according to the third embodiment, the relationship characteristic data is stored for each of the scanning conditions. In addition, when performing the successive approximation projection data correction processing, the calibration coefficient ($\alpha$, $\beta$) is calculated by reading the reference relationship characteristic data according to the scanning condition at the time of projection data measurement. Therefore, also for the projection data obtained by scanning under any scanning conditions, it is possible to maintain the noise reduction effect and the streak reduction effect constant.

In particular, the scanning conditions (scanning information value) are recorded for each scanning range (for example, for each view) at the time of scanning. Therefore, even if a plurality of scanning conditions or scanning parts are included in the projection data, it is possible to correct the projection data by calculating the calibration coefficient ($\alpha$, $\beta$) corresponding to the scanning conditions of each view or the like. Therefore, it is possible to obtain a uniform noise reduction effect and a streak reduction effect.

As described above, according to the X-ray CT apparatus 1 of the present invention, in the iterative processing including the noise reduction processing f1 and the signal strength maintenance processing f2 for preventing the generation of streaks, the reconstruction arithmetic device 221 calculates the correction coefficient β and the adjustment coefficient α for adjusting the application ratio of the noise reduction processing f1 and the signal strength maintenance processing f2 so that the desired amount of noise is obtained, and creates corrected projection data by performing the successive approximation projection data correction processing based on this calibration coefficient (α, β).

Therefore, it is possible to reduce streak artifacts generated around the high absorber on the image while reducing the amount of noise included in the image.

In each of the embodiments described above, when calculating the amount of streaks, the amount of streaks is calculated based on the reconstructed image. However, the method of calculating the amount of streaks is not limited thereto. Hereinafter, the method of calculating the amount of streaks will be described with reference to FIGS. 30 and 31.

Figure 30:
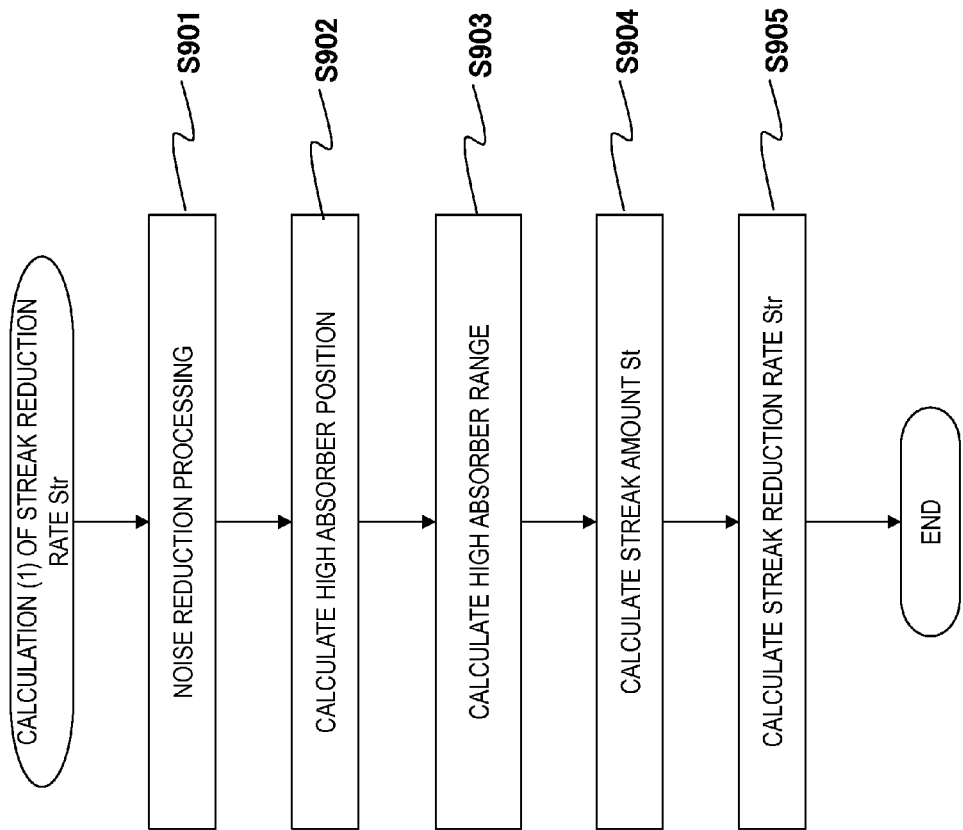
FIG. 30 is a flowchart showing the procedure of processing for calculating the streak reduction rate Str from an image.

FIG. 30 is a flowchart showing the procedure of calculating the amount of streaks around the high absorber on the image.

The reconstruction arithmetic device 221 acquires projection data, performs the noise reduction processing f1, and reconstructs the projection data after the noise reduction processing f1 (step S901). The reconstruction arithmetic device 221 sets a square (matrix) of a representative size on the obtained image, calculates an average value of CT values in the matrix, and stores the value. Then, the above-described matrix is moved by one pixel so as to cover all in the image, and an average value of the CT values in the matrix is calculated and stored. A position of the largest value among the stored values is assumed to be a high absorber position (step S902; calculation of a high absorber position).

The reconstruction arithmetic device 221 extracts an edge curve by fitting the high absorber in the matrix of lopt in an ellipse or a curve. Fitting is performed for a portion corresponding to a "high absorber" among the "high absorber", "low absorber", and "streaks" obtained by dividing the CT values in the matrix into three values. The reconstruction arithmetic device 221 applies a tangential line of the appropriate length on the edge curve, and sets a rectangular region where the tangential line is the long axis. Then, the reconstruction arithmetic device 221 calculates and stores an average value of the CT values in the rectangular region. This operation is performed so as to cover all on the edge curve, and an average value of the CT values in the rectangular region is calculated and stored. The reconstruction arithmetic device 221 sets a position of the largest value among the stored values as a streak position, and sets the value as a streak amount St1. On the image obtained by reconstructing the projection data (Raw_C) after correction by applying a rectangular region to the same position as the streak position described above, a streak amount St2 is calculated (step S904; calculation of the streak amount St).

The reconstruction arithmetic device 221 calculates the streak reduction rate Str from the ratio of the amounts of streaks St1 and St2 obtained in step S904 (step S905; calculation of the streak reduction rate Str).

The reconstruction arithmetic device 221 calculates the streak reduction rate Str from the ratio of the amounts of streaks St1 and St2 obtained in step S1003 (step S1004; calculation of the streak reduction rate Str).

As described above, it is possible to calculate streak artifacts on the image that are generated around the high absorber due to the noise reduction processing f1.

The reconstruction arithmetic device 221 may calculate the streak reduction rate Str from the projection data.

The method of calculating the streak reduction rate Str from the projection data will be described with reference to FIG. 31.

The reconstruction arithmetic device 221 calculates the largest CT value in the projection data of the scanning range, and sets the largest CT value as a high absorber CT value h. The range of projection data having values of k×h to h is assumed to be a high absorber representative region. k in this processing is a value of 0<k<1. For example, k=0.95. The reconstruction arithmetic device 221 sets, as a high absorber region, a region extending by dch in the channel direction toward the outside from the high absorber representative region (step S1001; calculation of the high absorber region).

dch is expressed by the following Equation (21). Here, fd is a function of the noise reduction rate r. dch increases in proportion to r.

$$dch = fd(r) \qquad (21)$$

The reconstruction arithmetic device 221 differentiates the projection data in the channel direction for all of the views, and calculates the absolute value. This data is set to differential projection data D. The reconstruction arithmetic device 221 calculates the largest value of the differential projection data D of all views, and sets the largest value as an edge differential value h_d. In addition, the reconstruction arithmetic device 221 sets the range of projection data having values of l×h_d to h_d as a high absorber edge region. l in this processing is a value of 0<l<1. For example, l=0.7. The high absorber region and the high absorber edge region are set as streak generation regions (step S1002; calculation of streak generation regions).

The reconstruction arithmetic device 221 sets an average value of the CT values in all streak generation regions on the projection data as the streak amount St1. In the same region as the streak generation region, the streak amount St2 is calculated on the projection data (Raw_C) after correction (step S1003; calculation of the streak amount St).

The reconstruction arithmetic device 221 calculates the streak reduction rate Str from the ratio of the amounts of streaks St1 and St2 obtained in step S603 (step S1004; calculation of the streak reduction rate Str).

As described above, it is possible to evaluate streak artifacts, which are generated around the high absorber due to the noise reduction processing f1, from the projection data. In this case, since it is not necessary to reconstruct an image, there is an advantage in that the amount of calculation is reduced.

While the preferred embodiments of the X-ray CT apparatus or the like according to the present invention have been described above, the present invention is not limited to the above embodiments. It is apparent to those skilled in the art that various changes and modifications can be made within the range of the technical idea disclosed in this specification, and it should be understood undoubtedly that they also belong to the technical range of the present invention.

REFERENCE SIGNS LIST

1: X-ray CT apparatus
3: object
10: scanner
20: operation unit
100: gantry
101: bed device
102: X-ray generator
103: X-ray detector
104: collimator device 105: high voltage generator
106: data acquisition system
107: driving device
200: central controller
201: input and output device
202: arithmetic device
211: display device
212: input device
213: storage device
41: target image quality setting section
42: number-of-iterations setting section
43: relationship characteristic calculating section
43a: feature amount extracting section
43b: shift amount calculating section
43c: reference relationship characteristic output section
43d: relationship characteristic update section
44: calibration coefficient calculating section
45: iterative processing section
46: end determination section
50: lower limb sectional image
50a: bone
50b: streak artifact
51, 52: profile of projection data
53: image without correction
54: image after noise reduction processing f1 55: image after adjustment processing f3
57, 58: ROI
61, 62: projection data
61a, 62a: projection data of high absorber
62b: correction region
63: difference between projection data before and after correction
64a, 64b: projection data of high absorber
66a, 66b: correction region
65: portion where pieces of projection data of high absorbers cross each other
7: feature region of projection data
71 to 74: corner
8: relationship characteristic data (r-Str data)
8a: reference relationship characteristic table (SD-St data)
80: calibration coefficient corresponding to desired image quality
81, 82, 83: shift characteristic data of feature amounts C1 to C3
85: updated relationship characteristic table
9: operation window
α: adjustment coefficient
β: correction coefficient
C1: first feature amount (area of feature region 7)
C2: second feature amount (shape of feature region 7)
C3: third feature amount (projection value of corners 71 to 74 of feature region 7)

The invention claimed is:

1. An X-ray CT apparatus, comprising:
an X-ray generator that emits X-rays from periphery of an object;
an X-ray detector that detects X-rays transmitted through the object;
a data acquisition system that acquires data detected by the X-ray detector;
a reconstruction arithmetic device that creates projection data by receiving the data acquired by the data acquisition system and reconstructs a CT image using the projection data; and
a display device that displays the CT image,
wherein the reconstruction arithmetic device includes:
a number-of-iterations setting section that sets the number of iterations of iterative processing for correcting the projection data;
a calibration coefficient calculating section that calculates a calibration coefficient for adjusting an application ratio of a first processing function and a second processing function having a different characteristic from the first processing function, the first and second processing functions being included in the iterative processing;
a successive approximation projection data correction processing section that creates corrected projection data by performing the iterative processing on the projection data based on the number of iterations and the calibration coefficient; and
an image reconstruction section that reconstructs the CT image using the corrected projection data.

2. The X-ray CT apparatus according to claim 1,
wherein the reconstruction arithmetic device further includes:
a relationship characteristic calculating section that calculates relationship characteristic data showing a relationship between a first and second image quality parameters and the calibration coefficient, a first image quality parameter being controlled by the first processing function and a second image quality parameter being controlled by the second processing function; and
a target image quality setting section that sets a target value for each of the first and second image quality parameters, and
the calibration coefficient calculating section calculates a calibration coefficient corresponding to the target value based on the relationship characteristic data.

3. The X-ray CT apparatus according to claim 2, further comprising:
a storage device that stores reference relationship characteristic data as a reference of the relationship characteristic data in advance,
wherein the calibration coefficient calculating section includes:
a feature amount extracting section that extracts a feature amount of the projection data;
a shift amount calculating section that calculates a shift amount of each of the first and second image quality parameters based on the feature amount; and
a relationship characteristic update section that calculates updated relationship characteristic data by updating the reference relationship characteristic data based on the shift amount, and
the calibration coefficient corresponding to the target value is calculated based on the updated relationship characteristic data.

4. The X-ray CT apparatus according to claim 3,
wherein the feature amount includes at least one of a first feature amount regarding a size of a feature region surrounded by a plurality of high absorber edges appearing in projection data, a second feature amount regarding a shape of the feature region, and a third feature amount regarding a magnitude of a projection value of the feature region.

5. The X-ray CT apparatus according to claim 1,
wherein the first processing function is a function regarding noise reduction, and the second processing function is a function regarding reduction of streak artifacts.

6. The X-ray CT apparatus according to claim 2,
wherein the relationship characteristic data is stored as a look-up table.

7. The X-ray CT apparatus according to claim 2,
wherein the relationship characteristic data is stored as an approximation function.

8. The X-ray CT apparatus according to claim 2,
wherein the relationship characteristic data is stored for each of the scanning conditions.

9. The X-ray CT apparatus according to claim 1, further comprising:
an input device that inputs a parameter or condition required to calculate a calibration coefficient,
wherein the calibration coefficient calculation section calculates the calibration coefficient based on the input a parameter or condition.

10. A reconstruction arithmetic device, comprising:
a number-of-iterations setting section that sets the number of iterations of iterative processing for correcting projection data;
a calibration coefficient calculating section that calculates a calibration coefficient for adjusting an application ratio of a first processing function and a second processing function having a different characteristic from the first processing function, the first and second processing functions being included in the iterative processing;
a successive approximation projection data correction processing section that creates corrected projection data by performing the iterative processing on the projection data based on the number of iterations and the calibration coefficient; and
an image reconstruction section that reconstructs a CT image using the corrected projection data.

11. A reconstruction arithmetic method, comprising:
a number-of-iterations setting step in which a reconstruction arithmetic device sets the number of iterations of iterative processing for correcting projection data;
a calibration coefficient calculation step in which the reconstruction arithmetic device calculates a calibration coefficient for adjusting an application ratio of a first processing function and a second processing function having a different characteristic from the first processing function, the first and second processing functions being included in the iterative processing;
a corrected projection data creation step in which the reconstruction arithmetic device creates corrected projection data by performing the iterative processing on the projection data based on the number of iterations and the calibration coefficient; and
a reconstruction step in which the reconstruction arithmetic device reconstructs a CT image using the corrected projection data.

* * * * *

UNITED STATES PATENT AND TRADEMARK OFFICE
CERTIFICATE OF CORRECTION

PATENT NO. : 9,592,026 B2
APPLICATION NO. : 14/778299
DATED : March 14, 2017
INVENTOR(S) : Yuta Ogura and Ryota Kohara Page 1 of 1

It is certified that error appears in the above-identified patent and that said Letters Patent is hereby corrected as shown below:

On the Title Page

Insert below Item (65) and above Item (51) the following Item (30) [Foreign Application Priority Data]:

--(30) Foreign Application Priority Data:
Apr. 8, 2013     (JP) .......................... 2013-080229--.

Signed and Sealed this
Sixteenth Day of May, 2017

Michelle K. Lee
*Director of the United States Patent and Trademark Office*